United States Patent [19]

Viaud et al.

[11] Patent Number: 5,714,495
[45] Date of Patent: Feb. 3, 1998

[54] PYRIDINE COMPOUNDS AS MELATONERGIC AGENTS

[75] Inventors: Marie-Claude Viaud, Versailles; Gérald Guillaumet, Orleans; Daniel Mazeas, Morancez; Hervé Vandepoel, Orleans; Pierre Renard, Versailles; Bruno Pfeiffer, Eaubonne; Philippe Delagrange, Issy les Moulineaux, all of France

[73] Assignee: Adir et Compagnie, Courbevoie, France

[21] Appl. No.: 631,234

[22] Filed: Apr. 12, 1996

[30] Foreign Application Priority Data

Apr. 14, 1995 [FR] France ................... 95 04504

[51] Int. Cl.$^6$ .............. A61K 31/44; C07D 471/04; C07D 491/084; C07D 513/04
[52] U.S. Cl. ............. 514/300; 514/301; 514/302; 546/113; 546/114; 546/115; 546/116
[58] Field of Search ................ 546/113, 114, 546/115, 116; 514/300, 301, 302

[56] References Cited

U.S. PATENT DOCUMENTS 5,541,228  7/1996  Takaki .................... 514/630
5,552,428  9/1996  Fraschini ................. 514/415

OTHER PUBLICATIONS

Krause D. M. et al., Society for Neuroscience, 1996, 22, No. 551.19, p. 1400.
Vacas et al., J. Pineal Res., 1992, 13, pp. 60–65.
Cagnacci et al., J. Pineal Res., 1997 22, pp. 16–19.
Viguerie–Bascands N. et al., Keystone Symposia, J3: The Adipose cell, Park City, UT, 1997, p. 22.
Bylesjö E.I. et al., International Journal of Eating Disorders, 1996, 20(4), pp. 443–446.
Ferrari F. et al., Biol. Psychiatry, 1990 37, pp. 1007–1020.
Mazzucchelli C., Molecular Brain Research, 1996 39 p. 117–126.
Brown G.M., CNS Drugs, 1995 3(3), pp. 209–226.
Stankov B., Neuroscience, 1993 52(2), pp. 459–468.
Leone M. et al., Cephalalgia, 1996 16, pp. 494–496.
Shui–Wang Ying et al., Eur. Journal of Pharmacology, 1993 246, pp. 89–96.
Laudon M. et al., Journal of clinical Endocrinology and Metabolism, 1996 81(4), pp. 1336–1342.
Lissoni P., British Journal of Cancer, 1996 74, pp. 1466–1468.

Primary Examiner—C. Warren Ivy
Assistant Examiner—Evelyn Huang
Attorney, Agent, or Firm—The Firm of Gordon W. Hueschen

[57] ABSTRACT

The invention relates to a compound selected from those of formula (I):

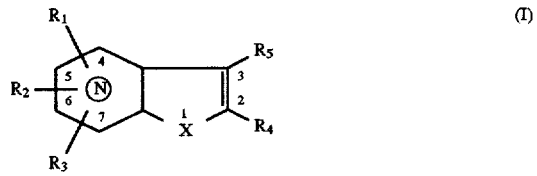

in which: $R_1$, $R_2$, $R_3$, $R_4$, $R_5$ and X are as defined in the description and medicinal product containing the same useful for treating a disorder of the melatoninergic system.

11 Claims, No Drawings

PYRIDINE COMPOUNDS AS MELATONERGIC AGENTS

The invention relates to novel pyridine compounds, to processes for their preparation and to the pharmaceutical compositions which contain them.

The invention describes novel pyridine compounds which prove to be powerful melatoninergic receptor ligands.

In the last ten years, many studies have demonstrated the fundamental role of melatonin(5-methoxy-N-acetyltryptamine) in controlling the circadian rhythm and endocrin functions, and the melatonin receptors have been characterized and located.

Besides their beneficial action on circadian rhythm disorders (J. Neurosurg 1985, 63, pp 321–341) and on sleeping disorders (Psychopharmacology, 1990, 100 pp 222–226), the ligands of the melatoninergic system possess advantageous pharmacological properties on the central nervous system, in particular anxiolytic and antipsychotic properties (Neuropharmacology of Pineal Secretions, 1990, 8 (3–4), pp 264–272) and analgesic properties (Pharmacopsychiat., 1987, 20, pp 222–223) as well as for the treatment of Parkinsons disease (J. Neurosurg 1985, 63, pp 321–341) and Alzheimer disease (Brain Research, 1990, 528, pp 170–174). Similarly, these compounds have shown activity on certain cancers (Melatonin - Clinical Perspectives, Oxford University Press, 1988, pp 164–165), on ovulation (Science 1987, 227, pp 714–720) arid on diabetes (Clinical endocrinology, 1986, 24, pp 359–364).

Compounds which make it possible to act on the melatoninergic system are thus excellent medicinal products for the clinician for the treatment of pathologies associated with disorders of the melatoninergic system.

N-[2-(1H-Pyrrolo[3,2-c]pyrid-3-yl)ethyl]acetamide is known from the literature (Farmaco Ed. Sci. 1964, 19, pp 741–750).

4-Methyl-1-phenylpyrrolo[2,3-b]pyridine derivatives are also known from the literature (Yakhontov L. N. et al: Chemical Abstracts, vol 64 (1) 1966 colonne 19584 a (Khim. Geterotsikl. Soedin., Akad. Nauk. Latv. SSR, 1966 (1) pp 80–4) and Chemical Abstracts, vol. 64 (1) 1966 column 5057d (Biol. Aktivn. Soedin. Akad. Nauk. SSR, 1965, pp 83–90), however, no pharmacological activity is mentioned in their respect, these compounds being presented as synthetic intermediates for obtaining 12-aza-β-carboline derivatives.

The invention relates to the compounds of formula (I):

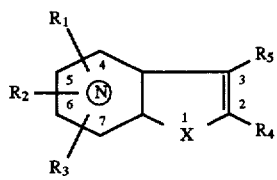

in which $R_1$, $R_2$, $R_3$ and $R_4$ represent, independently of each other, a hydrogen or a radical chosen from halogen, hydroxyl, Ra and —O—Ra; with Ra chosen from alkyl, alkyl substituted with one or more halogens, trialkylsilyl, alkenyl, alkynyl, cycloalkyl, cycloalkylalkyl, an/I, substituted an/I, arylalkyl and substituted arylalkyl;

$R_5$ represents a group of formula —A—B—Y in which
A represents a ($C_1$–$C_6$) alkylene chain which is unsubstituted or substituted with one or more alkyls,
B represents a group $B_1$, $B_2$ or $B_3$:

et 

in which Z represents an oxygen or a sulfur and $R_6$ represents a hydrogen or a radical chosen from alkyl, cycloalkyl, cycloalkylalkyl, aryl and arylalkyl, Y represents a radical $Y_1$ chosen from alkyl, alkyl substituted with one or more halogens, alkenyl, alkynyl, cycloalkyl and cycloalkylalkyl; Y may also represent a hydrogen when B represents a group $B_1$ or $B_2$, and X represents an oxygen, a sulfur or a group

in which $R_7$ represents a hydrogen or a radical chosen from alkyl, aryl, substituted aryl, arylalkyl and substituted arylalkyl; or $R_7$ represents a group of formula —A—B—Y as defined above and, in this case, $R_5$ represents a value chosen from those defined for $R_1$, $R_2$, $R_3$ and $R_4$, as defined above, with the proviso that the compound of formula (I) cannot be N-[2-(1H-pyrrolo[3,2-c]pyrid-3-yl)ethyl]acetamide, and that $R_7$ cannot represent a phenyl when the nitrogen of the pyridin ring of the formula (I) is in the 7-position of the heterocycle, $R_1$ is an alkyl group in the 4-position of the heterocycle and $R_2$, $R_3$ and $R_4$ represent hydrogens, it being understood that:
the terms "alkyl" and "alkoxy" denote linear or branched groups containing from 1 to 6 carbon atoms,
the terms "alkenyl" and "alkynyl" denote linear or branched unsaturated groups containing from 2 to 6 carbon atoms,
the term "cycloalkyl" denotes a group of 3 to 8 carbon atoms,
the term "aryl" denotes a phenyl, naphthyl or pyridyl radical,
the term "substituted" in reference to the expressions "aryl" and "arylalkyl" means that these groups may be substituted on the aromatic rings with one or more radicals chosen from halogen, alkyl, alkoxy, hydroxyl and alkyl subsitituted with one or more halogens;

the enantiomers and diastereoisomers thereof and the addition salts thereof with a pharmaceutically acceptable acid or base.

The invention relates particularly to the compounds of formula (I) in which, taken together or separately, $R_1$, $R_2$ and $R_3$ simultaneously represent hydrogens, one of the substituents $R_1$, $R_2$ and $R_3$ represents a radical chosen from halogen, alkoxy and alkyl and the other two represent hydrogens, A represents a methylene chain, A represents an ethylene chain, A represents a trimethylene chain, B represents a group —N(R$_6$)—C(=Z)—

B represents a group —N(R$_6$)—C(=Z)—NH—

B represents a group —C(=Z)—N(R$_6$)—

Z represents an oxygen,

Z represents a sulfur,

Y represents an alkyl,

Y represents a cycloalkyl,

X represents an oxygen,

X represents a sulfur, and X represents a group —N(R$_7$)—.

For example, the invention relates to the specific cases of compounds of formula (I) corresponding to the following formulae (1) to (11):

(1)

(2)

(3)

(4)

(5)

(6)

(7)

(8)

(9)

(10)

(11)

in which R$_1$, R$_2$, R$_3$, R$_4$, R$_7$, A, B and Y are as defined in formula (I).

The invention relates more particularly to the cases of compounds of formulae (1) to (11) in which R$_1$, R$_2$, R$_3$ and R$_4$ simultaneously represent hydrogens or one of the substituents R$_1$, R$_2$, R$_3$ or R$_4$ is a radical chosen from halogen, alkoxy and alkyl and the other remaining substituents R$_1$, R$_2$, R$_3$ or R$_4$ are hydrogens.

For example, the invention relates to the specific cases of the compounds of formula (I) corresponding to the following formulae (12) and (13):

(12)

(13)

in which R$_7$, B and Y are as defined in formula (I).

The alkyl radicals present in the formula (I) may be chosen in particular from methyl, ethyl, n-propyl, isopropyl, n-butyl, isobutyl, sec-butyl, tert-butyl, pentyl and hexyl, the alkoxy radicals present in the formula (I) may be chosen from methoxy, ethoxy, n-propoxy, isopropoxy, n-butoxy, iso-butoxy, sec-butoxy, tert-butoxy, pentyloxy and hexyloxy, the halogens present in the formula (I) may be chosen from bromine, chlorine, fluorine and iodine, the cycloalkyls present in the formula (I) may be chosen from cyclopropyl, cyclobutyl, cyclopentyl, cyclohexyl, cycloheptyl and cyclooctyl;

and the alkylene groups present in the formula (I) may be chosen from methylene, ethylene, trimethylene, tetramethylene, pentamethylene and hexamethylene.

Among the pharmaceutically acceptable acids which may be used to form an addition salt with the compounds of the invention, non-limiting examples which may be mentioned are hydrochloric acid, sulfuric acid, phosphoric acid, tartaric acid, malic acid, maleic acid, fumaric acid, oxalic acid, methanesulfonic acid, ethanesulfonic acid, camphoric acid and citric acid.

Among the pharmaceutically acceptable bases which may be used to form an addition salt with the compounds of the invention, non-limiting examples which may be mentioned are sodium hydroxide, potassium hydroxide, calcium hydroxide or aluminum hydroxide, alkali metal carbonates, alkaline-earth metal carbonates and organic bases such as triethylamine, benzylamine, diethanolamine, tert-butylamine, dicyclohexylamine and arginine.

The invention also relates to the process for the preparation of the compounds of formula (I), in which process, when B represents a group $B_1$ or $B_2$ as defined in the formula (I), an amine of formula (II):

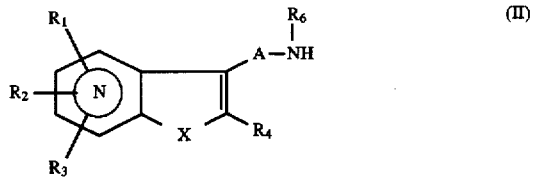

in which $R_1$, $R_2$, $R_3$, $R_4$, $R_6$, A and X are as defined in formula (I), is reacted either with a compound of formula (IIIa) or (IIIb):

it being possible for the anhydride (IIIb) to be mixed or symmetrical, in which $Y_1$ is as defined in formula (I) and Hal represents a halogen atom, so as to obtain the compounds of formula (I/a):

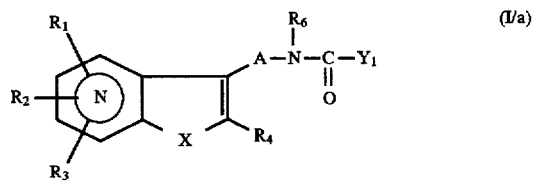

in which $R_1$, $R_2$, $R_3$, $R_4$, $R_6$, A, $Y_1$ and X are as defined above, which compound of formula (I/a) is then subjected to Lawesson's reagent to give the compounds of formula (I/b):

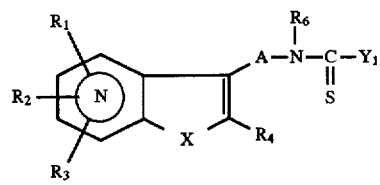

in which $R_1$, $R_2$, $R_3$, $R_4$, $R_6$, A, $Y_1$ and X are as defined above.

or with formic acid, to give a compound of formula (I/c):

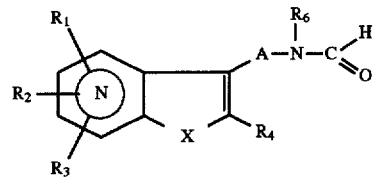

in which $R_1$, $R_2$, $R_3$, $R_4$, $R_6$, A and X are as defined above, or with a compound of formula (IV):

in which Y and Z are as defined in formula (I), so as to obtain the compounds of formula (I/d):

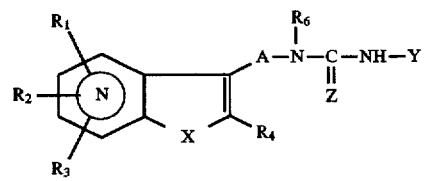

in which $R_1$, $R_2$, $R_3$, $R_4$, $R_6$, A, X, Y and Z are as defined above, and in which process, when B represents a group $B_3$ as defined in formula (I), a compound of formula (V):

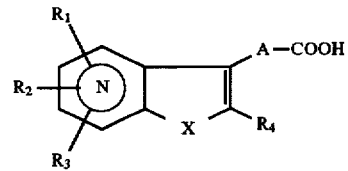

in which $R_1$, $R_2$, $R_3$, $R_4$, A and X are as defined in formula (I), is reacted with an amine of formula (VI):

in which $R_6$ and Y are as defined in formula (I), to give the compound of formula (I/e):

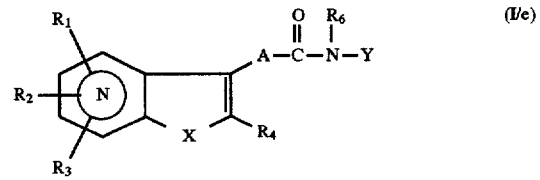

in which $R_1$, $R_2$, $R_3$, $R_4$, $R_6$, A, X and Y are as defined above, which compounds of formula (I/e) are subjected to Lawesson's reagent to give the compounds of formula (I/f):

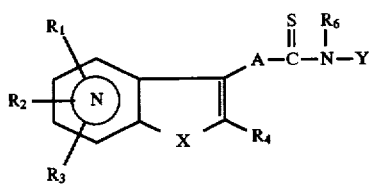 (I/f)

in which $R_1$, $R_2$, $R_3$, $R_4$, $R_6$, A, X and Y are as defined above, it being understood that, when $R_7$ as defined in formula (I) represents a group of formula —A—B—Y as defined in formula (I), the preparation process is similar to that described above, the reactants of formula (IIIa), (IIIb), formic acid and (IV), on the one hand, or (VI), on the other hand, react respectively with groups of formula —A—NH—$R_6$ or —A—COOH, attached to the 1-position of the pyrrolopyridine heterocycle present in the formula (I), it being possible for the compounds of formula (I) obtained to be:

- purified according to one or more purification methods chosen from crystallization, chromatography, extraction, filtration and passage through charcoal or resin,
- separated, where appropriate, in pure form or in the form of a mixture, into the possible enantiomers or diastereoisomers thereof,
- or salified with a pharmaceutically acceptable acid or base.

The invention also relates to the production of the compounds of formula (I/g), specific cases of the compounds of formula (I) in which $R_6$ is other than hydrogen, by alkylation of a compound of formula (I/h), a specific case of the compounds of formula (I) in which Re is a hydrogen.

The invention also relates to the process for the preparation of the compounds of formula (I), in which process a compound of formula (VII)

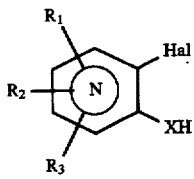 (VII)

in which $R_1$, $R_2$, $R_3$ and X are as defined in formula (I) and Hal represents a halogen atom, is condensed with a compound of formula (VIII):

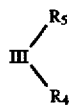 (VIII)

in which $R_4$ and $R_5$ are as defined in formula (I), it being possible for the compounds of formula (I) to be:
- purified according to one or more purification methods chosen from crystallization, chromatography, extraction, filtration and passage through charcoal or resin,
- separated, where appropriate, in pure form or in the form of a mixture, into the possible enantiomers or diastereoisomers thereof,
- or salified with a pharmaceutically acceptable acid or base.

For example, the invention relates to the process for the preparation of the compounds of formula (I'):

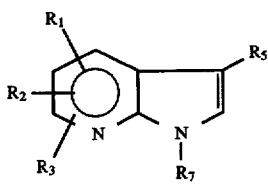 (I')

in which $R_1$, $R_2$, $R_3$, $R_5$ and $R_7$ are as defined in formula (I) in which process, when B represents a group $B_1$ or $B_2$ as defined in formula (I), an amine of formula (II'):

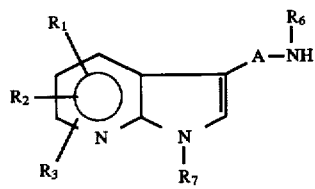 (II')

in which $R_1$, $R_2$, $R_3$, $R_6$, $R_7$ and A are as defined in formula (I), is reacted
either with a compound of formula (IIIa) or (IIIb):

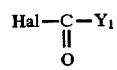 (IIIa)

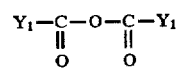 (IIIb)

it being possible for the anhydride (IIIb) to be mixed or symmetrical, in which $Y_1$ is as defined in formula (I) and Hal represents a halogen atom, so as to obtain the compounds of formula (I/a'):

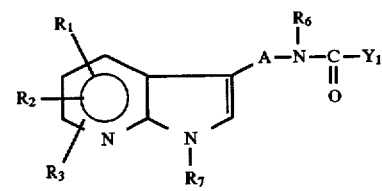 (I/a')

in which $R_1$, $R_2$, $R_3$, $R_6$, $R_7$, A and $Y_1$ are as defined above, which compound of formula (I/a') is then subjected to Lawesson's reagent to give the compounds of formula (I/b'):

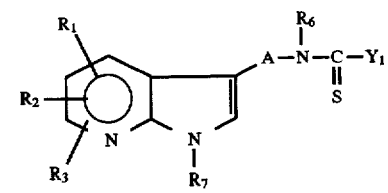 (I/b')

in which $R_1$, $R_2$, $R_3$, $R_6$, $R_7$, A and $Y_1$ are as defined above, or with formic acid, to give a compound of formula (I/c'):

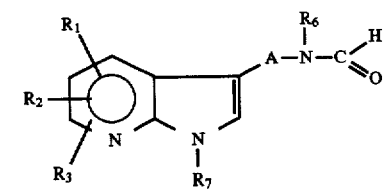 (I/c')

in which $R_1$, $R_2$, $R_3$, $R_6$, $R_7$ and A are as defined above, or with a compound of formula (IV):

$$Z=C=N-Y \quad \text{(IV)}$$

in which Y and Z are as defined in formula (I), so as to obtain the compounds of formula (I/d'):

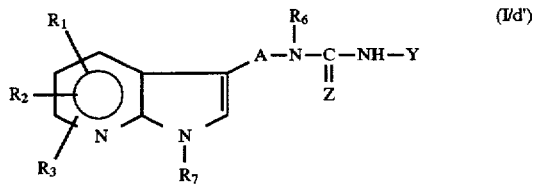

in which $R_1$, $R_2$, $R_3$, $R_6$, A, Y and Z are as defined above, and in which process, when B represents a group $B_3$ as defined in formula (I), a compound of formula (V'):

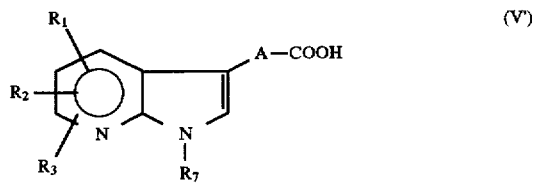

in which $R_1$, $R_2$, $R_3$, $R_7$ and A are as defined in formula (I), is reacted with an amine of formula (VI):

in which $R_6$ and Y are as defined in formula (I), to give the compound of formula (I/e'):

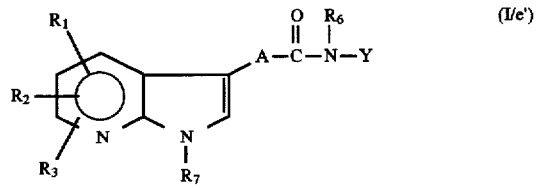

in which $R_1$, $R_2$, $R_3$, $R_6$, $R_7$, A and Y are as defined above, which compounds of formula (I/e') are subjected to Lawesson's reagent to give the compounds of formula (I/f'):

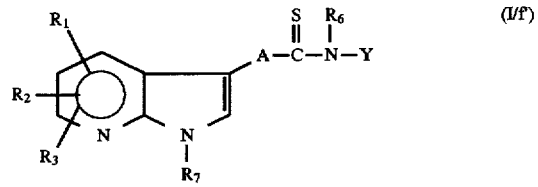

$R_1$, $R_2$, $R_3$, $R_6$, $R_7$, A and Y are as defined above, the compounds of formulae (I/a'), (I/b'), (I/c'), (I/d'), (I/e') and (I/f') together forming the compounds of formula (I'), which compounds of formula (I') are, where appropriate, purified according to one or more purification methods chosen from crystallization, chromatography, extraction, filtration and passage through charcoal or resin, separated, where appropriate, in pure form or in the form of a mixture, into the possible enantiomers or diastereoisomers thereof, or salified with a pharmaceutically acceptable acid or base.

The invention also relates to the production of the compounds of formula (I/g'), specific cases of the compounds of formula (I') in which $R_6$ is other than hydrogen, by alkylation of a compound of formula (I/h'), a specific case of the compounds of formula (I') in which $R_6$ is a hydrogen.

For example, the invention relates to the process for the preparation of the compounds of formula (I"):

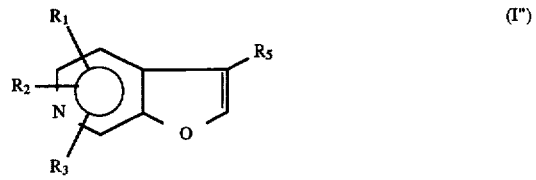

in which $R_1$, $R_2$, $R_3$ and $R_5$ are as defined in formula (I) in which process, when B represents a group $B_1$ or $B_2$ as defined in formula (I), an amine of formula (II"):

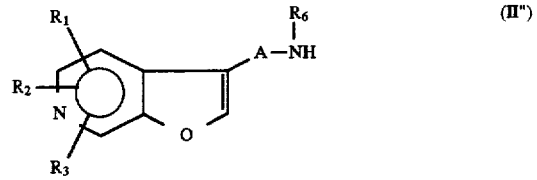

in which $R_1$, $R_2$, $R_3$, $R_6$ and A are as defined in formula (I), is reacted either with a compound of formula (IIIa) or (IIIb):

it being possible for the anhydride (IIIb) to be mixed or symmetrical, in which $Y_1$ is as defined in formula (I) and Hal represents a halogen atom, so as to obtain the compounds of formula (I/a"):

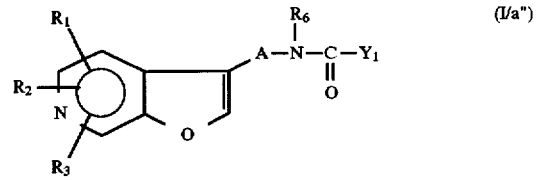

in which $R_1$, $R_2$, $R_3$, $R_6$, A and $Y_1$ are as defined above, which compound of formula (I/a) is then subjected to Lawesson's reagent to give the compounds of formula (I/b"):

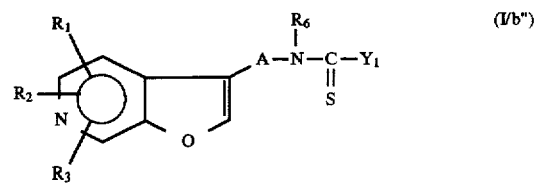

in which $R_1$, $R_2$, $R_3$, $R_6$, A and $Y_1$ are as defined above, or with formic acid, to give a compound of formula (I/c"):

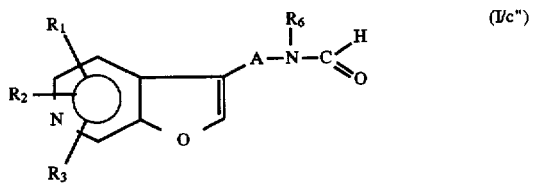
(I/c")

in which $R_1$, $R_2$, $R_3$, $R_6$ and A are as defined above, or with a compound of formula (IV):

$$Z=C=N-Y \quad (IV)$$

in which Y and Z are as defined in formula (I), so as to obtain the compounds of formula (I/d"):

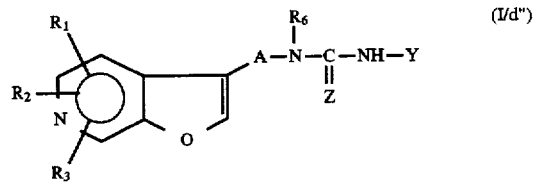
(I/d")

in which $R_1$, $R_2$, $R_3$, $R_6$, A, Y and Z are as defined above, and in which process, when B represents a group $B_3$ as defined in formula (I), a compound of formula (V"):

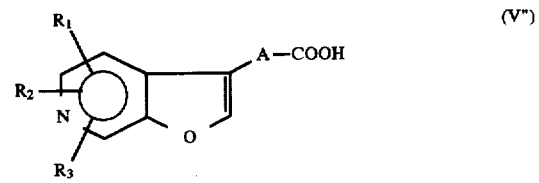
(V")

in which $R_1$, $R_2$, $R_3$ and A are as defined in formula (I), is reacted with an amine of formula (VI):

(VI)

in which $R_6$ and Y are as defined in formula (I), to give the compound of formula (I/e"):

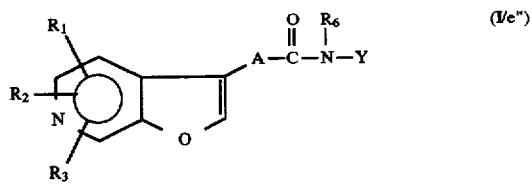
(I/e")

in which $R_1$, $R_2$, $R_3$, $R_6$, A and Y are as defined above, which compounds of formula (I/e") are subjected to Lawesson's reagent to give the compounds of formula (I/f"):

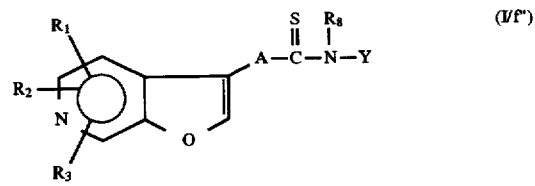
(I/f")

$R_1$, $R_2$, $R_3$, $R_6$, A, X and Y are as defined above, the compounds of formulae (I/a"), (I/b"), (I/c"), (I/d"), (I/e") and (I/f") together forming the compounds of formula (I")

which compounds of formula (I") are, where appropriate, purified according to one or more purification methods chosen from crystallization, chromatography, extraction, filtration and passage through charcoal or resin, separated, where appropriate, in pure form or in the form of a mixture, into the possible enantiomers or diastereoisomers thereof, or salified with a pharmaceutically acceptable acid or base.

The invention also relates to the production of the compounds of formula (I/g"), specific cases of the compounds of formula (I") in which $R_6$ is other than hydrogen, by alkylation of a compound of formula (I/h"), a specific case of the compounds of formula (I") in which $R_6$ is a hydrogen.

The invention also relates to the process for the preparation of the compounds of formula (I/i), a specific case of the compounds of formula (I):

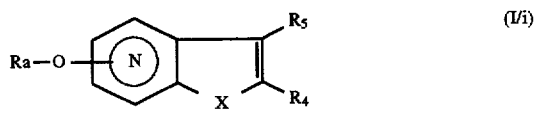
(I/i)

in which Ra, $R_4$, $R_5$ and X are as defined in formula (I), by grafting the radical Ra onto a compound of formula (I/j):

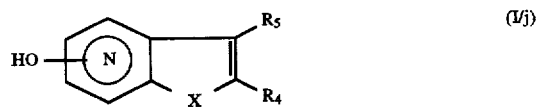
(I/j)

in which $R_4$, $R_5$ and X are as defined above, which compounds of formula (I/i) are, where appropriate, purified according to one or more purification methods chosen from crystallization, chromatography, extraction, filtration and passage through charcoal or resin, separated, where appropriate, in pure form or in the form of a mixture, into the possible enantiomers or diastereoisomers thereof, or salified with a pharmaceutically acceptable acid or base.

The grafting of the radical Ra is performed, for example, using a compound of formula (VII):

$$Ra-W \quad (VII)$$

in which Ra is as defined above and W represents a halogen or a leaving group.

The compounds of formula (I/j):

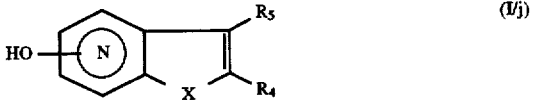
(I/j)

in which $R_4$, $R_5$ and X are as defined in formula (I) may be obtained by decarboxylation of the corresponding alkoxylated compound.

The abovementioned decarboxylation may be performed, for example, by the action of $BBr_3$ or a mixture $AIX"_3$, $R_bSH$ in which X" is a halogen and Rb is an alkyl.

The invention also relates to the process for the preparation of the compounds of formula (I/k), a specific case of the compounds of formula (I):

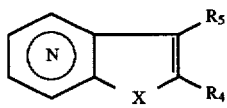 (I/k)

in which $R_4$, $R_5$ and X are as defined in formula (I), by acidic treatment of a compound of formula (I/l), a specific case of the compounds of formula (I):

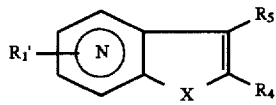 (I/l)

in which $R_4$, $R_5$ and X are as defined above and $R_1$, is a halogen atom, which compounds of formula (I/k) are, where appropriate,

- purified according to one or more purification methods chosen from crystallization, chromatography, extraction, filtration and passage through charcoal or resin,
- separated, where appropriate, in pure form or in the form of a mixture, into the possible enantiomers or diastereoisomers thereof,
- or salified with a pharmaceutically acceptable acid or base.

The invention also relates to the process for the preparation of the compounds of formula (I/k"), a specific case of the compounds of formula (I):

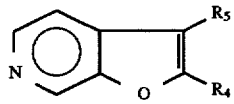 (I/k")

in which $R_4$ and $R_5$ are as defined in formula (I), by acidic treatment of a compound of formula (I/l"), a specific case of the compounds of formula (I):

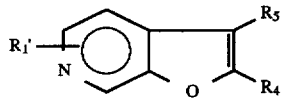 (I/l")

in which $R_4$ and $R_5$ are as defined above and $R_1'$ is a halogen atom, which compounds of formula (I/k") are, where appropriate,

- purified according to one or more purification methods chosen from crystallization, chromatography, extraction, filtration and passage through charcoal or resin,
- separated, where appropriate, in pure form or in the form of a mixture, into the possible enantiomers or diastereoisomers thereof,
- or salified with a pharmaceutically acceptable acid or base.

The starting materials used in the processes described above are either commercial or are accessible to those skilled in the art according to the literature and according to the preparation examples given below.

The compounds of formula (II) are accessible, for example, to those skilled in the art by reduction of a nitro compound of formula (II/a):

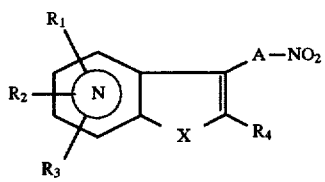 (II/a)

in which $R_1$, $R_2$, $R_3$, $R_4$, A and X are as defined in formula (I) or by hydrogenation of a compound of formula (II/b):

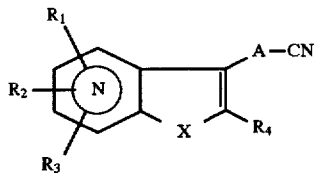 (II/b)

in which $R_1$, $R_2$, $R_3$, $R_4$ and X are as defined in formula (I) and A' represents a $(C_1-C_5)$alkylene chain which is unsubstituted or substituted with one or more alkyls.

The compounds of formula (II') are thus accessible, for example, to those skilled in the art by reduction of a nitro compound of formula (II/a'):

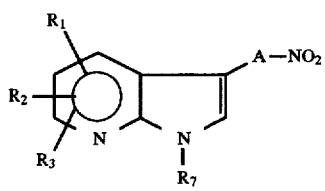 (II/a')

in which $R_1$, $R_2$, $R_3$, $R_7$ and A are as defined in formula (I) or by hydrogenation of a compound of formula (II/b'):

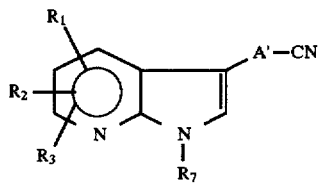 (II/b')

in which $R_1$, $R_2$, $R_3$ and $R_7$ are as defined in formula (I) and A' represents a $(C_1-C_5)$alkylene chain which is unsubstituted or substituted with one or more alkyls.

The compounds of formula (II") are accessible, for example, to those skilled in the art by reduction of a nitro compound of formula (II/a"):

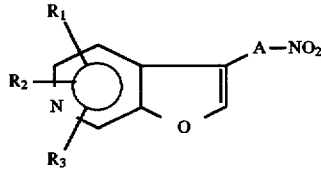 (II/a")

in which $R_1$, $R_2$, $R_3$ and A are as defined in formula (I) or by hydrogenation of a compound of formula (II/b"):

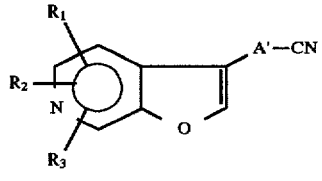 (II/b")

in which $R_1$, $R_2$ and $R_3$ are as defined in formula (I) and A' represents a $(C_1-C_5)$ alkylene chain which is unsubstituted or substituted with one or more alkyls.

The compounds of formula (II/a) are, for example, readily accessible when $R_4$ is a hydrogen, by reduction of a compound of formula (II/c):

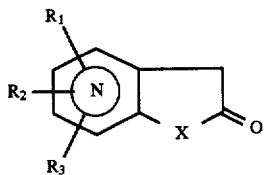
(II/c)

in which $R_1$, $R_2$, $R_3$ and X are as defined in formula (I), to give a compound of formula (II/d):

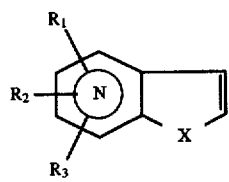
(II/d)

in which $R_1$, $R_2$, $R_3$ and X are as defined above, which compound is then reacted with N,N-dimethylformamide to give the compound of formula (II/e):

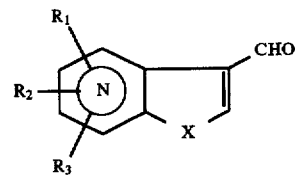
(II/e)

in which $R_1$, $R_2$, $R_3$, and X are as defined above, which compound is then subjected to the action of the nitro compound of formula (II/f):

$A_2-NO_2$     (II/f)

in which $A_2$ is a $(C_1-C_5)$alkyl radical which is unsubstituted or substituted with one or more alkyls, to give, optionally after hydrogenation, a compound of formula (II/a) as defined above.

The compounds of formula (II/a') are, for example, readily accessible by reduction of a compound of formula (II/c'):

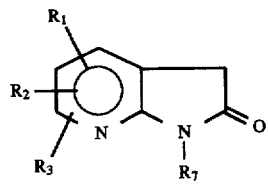
(II/c')

in which $R_1$, $R_2$, $R_3$ and $R_7$ are as defined in formula (I), to give a compound of formula (II/d'):

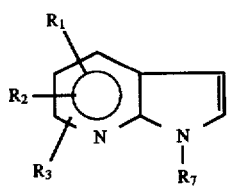
(II/d')

in which $R_1$, $R_2$, $R_3$ and $R_7$ are as defined above, which compound is then reacted with N,N-dimethylformamide to give the compound of formula (II/e'):

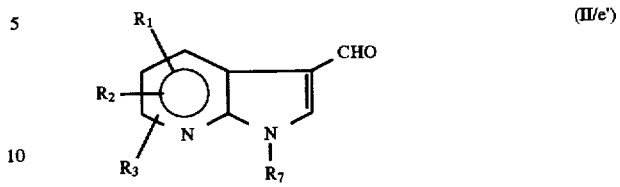
(II/e')

in which $R_1$, $R_2$, $R_3$ and $R_7$ are as defined above, which compound is then subjected to the action of the nitro compound of formula (II/f):

$A_2-NO_2$     (II/f)

in which $A_2$ is a $(C_1-C_5)$alkyl radical which is unsubstituted or substituted with one or more alkyls, to give, optionally after hydrogenation, a compound of formula (II/a') as defined above.

The compounds of formula (II/b) when A represents an ethylene, are also readily accessible to those skilled in the art by cyclization of a compound of formula (II/g):

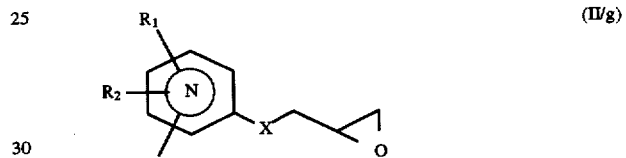
(II/g)

in which $R_1$, $R_2$, $R_3$ and X are as defined in formula (I), to give a compound of formula (II/h):

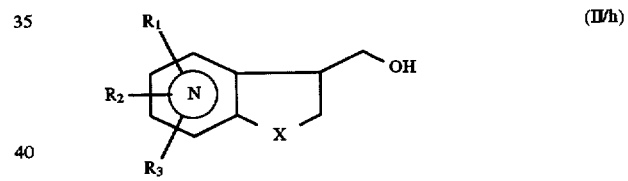
(II/h)

in which $R_1$, $R_2$, $R_3$ and X are as defined above, which compound is then subjected to the action of tosyl chloride to give a compound of formula (II/i):

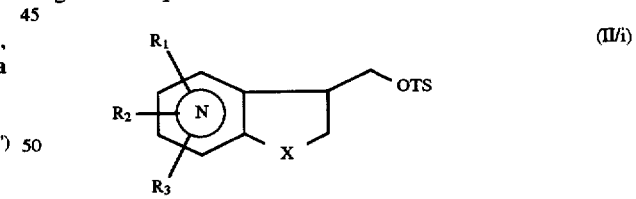
(II/i)

in which $R_1$, $R_2$, $R_3$ and X are as defined above and Ts represents a tosyl group, which compound is then reacted with 1,4-diazacyclo[2-2-2]octane to give a compound of formula (II/j):

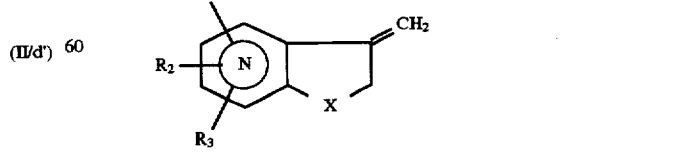
(II/j)

in which $R_1$, $R_2$, $R_3$ and X are as defined above, which compound is then halogenated to give a compound of formula (II/k):

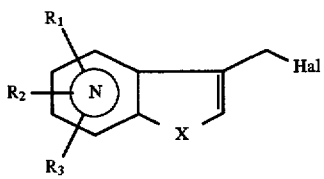
(II/k)

in which $R_1$, $R_2$, $R_3$ and X are as defined above and Hal represents a halogen atom, of which compound the corresponding cyano derivative of formula (II/b) in which A represents an ethylene chain:

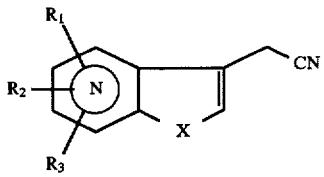
(II/b)

in which $R_1$, $R_2$, $R_3$ and X are as defined above, is prepared.

The compounds of formula (II/b"), when A represents an ethylene, are, for example, readily accessible to those skilled in the art by cyclization of a compound of formula (II/g"):

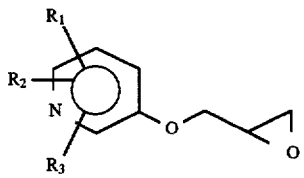
(II/g")

in which $R_1$, $R_2$ and $R_3$ are as defined in formula (I), to give a compound of formula (II/h"):

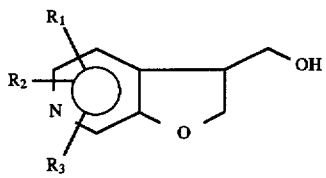
(II/h")

in which $R_1$, $R_2$ and $R_3$ are as defined above, which compound is then subjected to the action of tosyl chloride to give a compound of formula (II/i"):

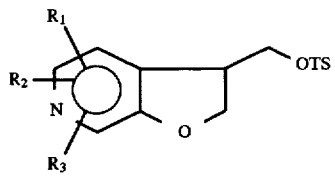
(II/i")

in which $R_1$, $R_2$ and $R_3$ are as defined above and Ts represents a tosyl group, which compound is then reacted with 1,4-diazacyclo[2-2-2]octane to give a compound of formula (II/j"):

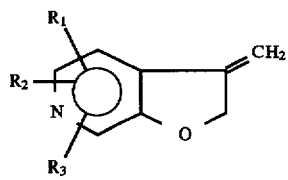
(II/j")

in which $R_1$, $R_2$ and $R_3$ are as defined above, which compound is then halogenated to give a compound of formula (II/k"):

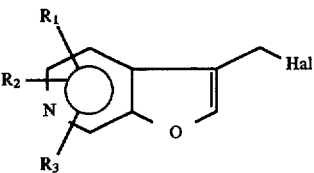
(II/k")

in which $R_1$, $R_2$ and $R_3$ are as defined above and Hal represents a halogen atom, of which compound the corresponding cyano derivative of formula (II/b") in which A represents an ethylene chain:

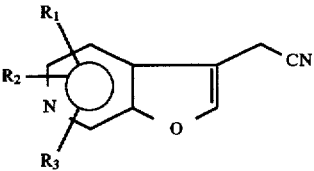
(II/b")

in which $R_1$, $R_2$ and $R_3$ are as defined above, is prepared.

The compounds of formula (I) possess pharmacological properties which are very advantageous for the clinician.

The compounds of the invention and the pharmaceutical compositions containing them prove to be useful for the treatment of disorders of the melatoninergic system.

Pharmacological study of the derivatives of the invention has in effect shown that they were not toxic, were endowed with a selective and very high affinity for the melatonin receptors and possessed considerable activity on the central nervous system and, in particular, therapeutic properties on sleeping disorders, anxiolytic, antipsychotic and analgesic properties and therapeutic properties on microcirculation were detected. The products of the invention are useful in the treatment of stress, sleeping disorders, anxiety, seasonal depressions, cardiovascular pathologies, insomnia and fatigue due to time zone changes, schizophrenia, panic attacks, melancholia, appetite disorders, psoriasis, obesity, insomnia, psychotic disorders, epilepsy, Parkinson's disease, senile dementia, various disorders associated with normal or pathological aging, migraine, memory losses, Alzheimer's disease and disorders of cerebral circulation. In another field of activity, it appears that the products of the invention possess inhibitory properties on ovulation and immunomodulatory properties and that they are capable of being used in anticancer treatment.

The compounds will preferably be used in the treatment of seasonal depressions, sleeping disorders, cardiovascular pathologies, insomnia and fatigue due to time zone changes, appetite disorders and obesity.

For example, the compounds will be used in the treatment of seasonal depressions and sleeping disorders.

The subject of the present invention is also the pharmaceutical compositions containing a compound of formula (I), or one of the addition salts thereof with a pharmaceutically acceptable acid or base, in combination with one or more pharmaceutically acceptable excipients.

Among the pharmaceutical compositions according to the invention which may be mentioned more particularly are those which are suitable for oral, parenteral, nasal, per- or transcutaneous, rectal, perlingual, ocular or respiratory administration and, in particular, simple or coated tablets, sublingual tablets, sachets, packets, gelatin capsules, glossettes, lozenges, suppositories, creams, ointments, dermal gels and drinkable or injectable ampules.

The dosage varies according to the sex, age and weight of the patient, the route of administration, the nature of the therapeutic indication, or on treatments which are possibly combined therewith, and ranges between 0.1 mg and 1 g per 24 hours, more particularly between 1 and 100 mg, for example between 1 and 10 mg.

The examples which follow illustrate the invention without, however, limiting it in any way.

PREPARATION 1: 3-(2-AMINOETHYL)-5-METHOXY-1-METHYLPYRROLO[2,3-b]PYRIDINE

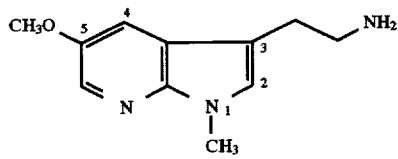

Stage A: 1-methylpyrrolo[2,3-b]pyridine

Pyrrolo[2,3-b]pyridine (2.00 g; 16.93 mmol) is dissolved in dimethylformamide (DMF) (15.0 cm$^3$), under argon atmosphere. Sodium hydride (60% in oil) (0.96 g; 40.0 mmol; 1.5 eq.) is added, at 0° C. and over a period of 30 min. After stirring for 30 min at 0° C., iodomethane (1.49 cm$^3$; 24.02 mmol; 1.5 eq.) is added dropwise. After warming to room temperature the reaction medium is left stirring for 1 h. The dimethylformamide is evaporated off under reduced pressure and the residue is taken up in water and extracted with dichloromethane. Purification on a column of silica (petroleum ether (PE)): (ethyl acetate (EtOAc)) (7:3) allows the title compound to be isolated in a yield of 99%. This product is in the form of an orange oil.

INFRARED (IR) SPECTROSCOPIC ANALYSIS (film): ν=1597 cm$^{-1}$ (C=C, Ar)

NMR SPECTROSCOPIC ANALYSIS ($^1$H NMR CDCl$_3$))

δ(ppm) 3.85 (s, 3H, CH$_3$), 6.40 (d, 1 H, H-3, J$_{3-2}$=3.3 Hz), 7.01 (dd, 1H, H-5, J$_{5-4}$=7.4 Hz, J$_{5-6}$=5.2 Hz), 7.13 (d, 1H, H-2, J$_{2-3}$=3.3 Hz), 7.85 (d, 1H, H-4, J$_{4-5}$=7.4 Hz), 8.29 (d, 1H, H-6, J$_{6-5}$=5.2 Hz).

Stage B: 3,3-dibromo-1-methyl-2-oxo-2,3-dihydropyrrolo[2,3-b]pyridine

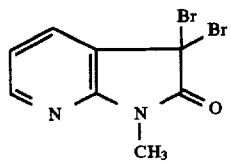

To a solution of the compound obtained in the above stage (5.59 g; 42.3 mmol) in tert-butanol (80 cm$^3$) is added pyridinium perbromate (40.58 g; 127.0 mmol; 3.0 eq.). The medium is stirred at room temperature for 2 h. The solvents are concentrated by evaporation under reduced pressure and the crude product is taken up in water and then extracted with ethyl acetate. After evaporation, an orange solid is obtained in a yield of 93%.

Melting point (m.p.): 180° C.

IR (KBr): ν=1738 cm$^{-1}$ (C=O).

$^1$H NMR (CDCl$_3$) δ(ppm): 3.33 (s, 3H, CH$_3$), 7.11 (dd, 1H, H-5, J$_{5-4}$=7.4 Hz, J$_{5-6}$=5.2 Hz), 7.85 (d, 1H, H-4, J$_{4-5}$=7.4 Hz), 8.27 (d, 1H, H-6, J$_{6-5}$=5.2 Hz).

Stage C: 3,3,5-tribromo-1-methyl-2-oxo-2,3-dihydropyrrolo[2,3-b]pyridine

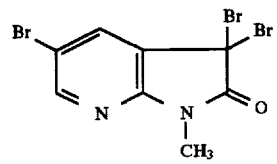

α) synthesis from the compound obtained in Stage B

The compound obtained in Stage B (12.46 g; 40.7 mmol) is dissolved in DMF (50 cm$^3$). After dropwise addition of bromine (4.17 cm$^3$; 81.4 mmol; 2 eq.), the reaction medium is left stirring for 15 h at room temperature. After evaporation of the solvent under reduced pressure, the product is taken up in water and then extracted with dichloromethane. Once the solvent has been evaporated off, the orange solid is washed with petroleum ether. After drying, the title compound is obtained in a yield of 85%.

β) synthesis from the compound obtained in Stage A

The compound obtained in Stage A (2.00 g; 15.1 mmol) is dissolved in tert-butanol (132 cm$^3$). An equivalent amount of water (132 cm$^3$) is added slowly. Bromine (9.28 cm$^3$; 181.2 mmol; 12.0 eq.) is added dropwise by means of a dropping funnel. After stirring for 24 h at room temperature, the tert-butanol is removed by evaporation under reduced pressure. The mixture is taken up in NaHCO$_3$ solution to neutral pH and is then filtered. After drying, the title compound is obtained in a yield of 91%.

m.p.=210° C.

IR (KBr): ν=1747 cm$^{-1}$ (C=O)

$^1$H NMR (CDCl$_3$) δ(ppm): 3.33 (s, 3H, CH$_3$), 7.95 (d, 1H, H-4, J$_{4-6}$=2.2 Hz), 8.31 (d, 1H, H-6, J$_{6-4}$=2.2 Hz).

Stage D: 5-bromo-1-methyl-2-oxo-2,3-dihydropyrrolo[2,3-b]pyridine

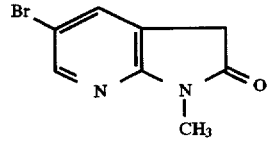

The compound obtained in the above stage (0.327 gr; 0.85 mmol) is dissolved in acetic acid (8 cm$^3$). Zinc (4.3 g; 8.5 mmol; 10 eq). is added, at room temperature and under argon. After stirring for 30 min at the same temperature, the reaction medium is filtered and then evaporated under reduced pressure. The crude product is extracted with ethyl acetate at neutral pH and then purified on a column of silica (PE: EtOAc 7:3). The title compound is obtained in a yield of 98% in the form of an orange solid.

m.p.=149° C.

IR (KBr): ν=1713 cm$^{-1}$ (C=O).

$^1$H NMR (CDCl$_3$) δ=3.28 (s, 3H, CH$_3$), 3.55 (s, 2H, CH$_2$), 7.59 (s, 1H, H-4), 8.25 (s, 1H, H-6).

Stage E: 5-bromo-1-methylpyrrolo[2,3-b]pyridine

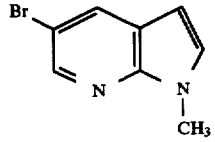

To 2 g (8.81 mmol) of the compound obtained in the above stage in solution in 40 cm$^3$ of anhydrous tetrahydrofuran (THF) are added dropwise 26.4 cm$^3$ (52.85 mmol; 6 eq.) of borane-dimethyl sulfide complex in solution in THF (2M). After refluxing for 2 h, the solvent is evaporated off and the reaction crude is taken up in 20 cm³ of methanol and 30 cm³ of 2N HCl. After refluxing for 30 min, the methanol is evaporated off and the medium is then neutralized with saturated sodium bicarbonate solution. The product is extracted with dichloromethane. The organic phase is dried over magnesium sulfate and then concentrated. The reaction crude is used directly in the oxidation step.

4.72 g (17.61 mmol) of manganese (III) acetate dihydrate are suspended in 77 cm³ of glacial acetic acid. To this suspension is added the above reaction crude in solution of 81 cm³ of glacial acetic acid. After 1 h at 75° C., the solvent is evaporated. The medium is hydrolyzed, neutralized with saturated sodium bicarbonate solution and then extracted with ethyl acetate, dried over magnesium sulfate and concentrated. After purification on a column of silica gel (eluent: $CH_2Cl_2$), the title product is obtained in the form of a light-yellow solid (1.38 g).

Yield: 74%
m.p.=48° C.
IR (KBr): $v$=3015 cm⁻¹ (C=C), $v$=1575 cm⁻¹ (C=C)
¹H NMR (CDCl₃): δ3.87 (s, 3H, CH₃), 6.39 (d, 1H, $J_{2-3}$=3.3 Hz, H-3), 7.18 (d, 1H, $J_{3-2}$=3.3 Hz, H-2), 8.01 (d, 1H, $J_{4-6}$=2.2 Hz, H-4), 8.34 (d, 1H, $J_{6-4}$=2.2 Hz, H-6).

Stage F: 1-methyl-5-methoxypyrrolo[2,3-b]pyridine

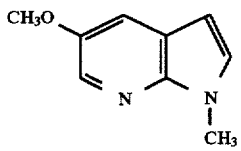

To 1.37 g (6.49 mmol) of the compound obtained in the above stage in solution in 23.6 cm³ of methanol and 36.5 cm³ of anhydrous DMF are added 18.6 g (344.02 mmol) of sodium methoxide and 1.86 g (12.98 mmol) of copper bromide. After refluxing for 1 h the solvents are removed under vacuum and the reaction crude is hydrolyzed with 50 cm³ of water and then neutralized with hydrochloric acid solution (6N). The product is extracted with dichloromethane. The organic phase is dried over magnesium sulfate and then concentrated. After purification on a column of silica (eluent: EtOAc: PE, 1:1), 930 mg of expected product are obtained in the form of a yellow liquid.

Yield: 88%
IR (NaCl): $v$=3100 cm⁻¹ (C=C), $v$=1590 cm⁻¹ (C=C)
¹H NMR (CDCl₃): δ3.86 (s, 3H, CH₃), 3.88 (s, 3H, CH₃), 6.36 (d, 1H, $J_{3-2}$=3.3 Hz, H-3), 7.15 (d, 1H, $J_{2-3}$=3.3 Hz, H-2), 7.41 (d, 1H, $J_{4-6}$=2.7 Hz, H-4), 8.12 (d, 1H, $J_{6-4}$=2.7 Hz, H-6).

Stage G: 3-formyl-5-methoxy-1-methylpyrrolo[2,3-b]pyridine

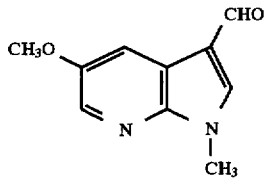

To 20.6 cm³ of DMF cooled to 0° C. are added slowly, without increasing the temperature, 1.09 cm³ (1.80 g; 11.73 mmol) of phosphorus oxychlodde, followed, still dropwise by 1.73 g (10.67 mmol) of the compound obtained in the above stage in solution in 17 cm³ of DMF. After 15 min at 80° C., the solvent is evaporated off and the reaction crude is hydrolyzed with water, neutralized with sodium hydroxide solution (50%) and then extracted with ethyl acetate. The organic phase is dried over magnesium sulfate and then concentrated. After purification on a column of silica gel (eluent: EtOAc) and then recrystallization in a cyclohexane/isopropanol mixture (60 cm³/5 cm³), the title aidehyde is obtained in the form of a white solid.

Yield: 71%
m.p.=105°–106° C.
IR (KBr) $v$=3100 cm⁻¹ (C=C), $v$=1660 cm⁻¹ (C=O)
¹H NMR (CDCl₃): δ3.92 (s, 3H, CH₃), 3.95 (s, 3H, CH₃), 7.79 (s, 1H, H-2), 8.06 (d, 1H, $J_{4-6}$=2.9 Hz, H-4), 8.19 (d, 1H, $J_{6-4}$=2.9 Hz, H-6), 9.95 (s, 1H, CHO).

Stage H: 5-methoxy-1-methyl-3-(2-nitrovinyl)-pyrrolo[2,3-b]pyridine

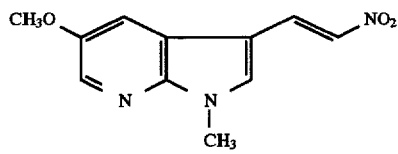

1.44 g (7.55 mmol) of the compound obtained in the above stage are dissolved in 36 cm³ of nitromethane. 1.16 g (18.93 mmol) of dry ammonium acetate are added thereto and the mixture is then maintained at 120° C. for 3 h 30. After cooling completely, the product is precipitated in the medium and is then filtered off on a sinter funnel and washed several times with ether. 1.47 g of a yellow solid are obtained.

Yield: 83%
m.p.=185° C.
IR (KBr): $v$=1610 cm⁻¹ (NO₂)
¹H NMR(CDCl₃): δ3.93 (s, 3H, CH₃), 3.95 (s, 3H, CH₃), 7.49 (d, 1H, $J_{4-6}$=2.6 Hz, H-4), 7.63 (s, 1H, H-2), 7.65 (d, 1H, J=14.2 Hz, CH), 8.20 (d, 1H, J=14.2 Hz, CH), 8.21 (d, 1H, $J_{6-4}$=2.6 Hz, H-6).

Stage I: 5-methoxy-1-methyl-3-(2-nitroethyl)-pyrrolo[2,3-b]pyridine

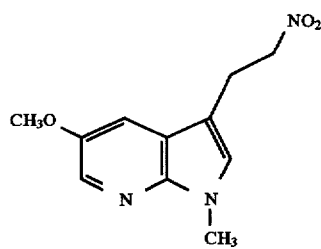

To 100 mg (4.29 10⁻⁴ mmol) of the compound obtained in the above stage in solution in 7.8 cm³ of chloroform and 2.7 cm³ of isopropanol are added 215 mg of silica (230–400 mesh) followed by portionwise addition of 40 mg (1.07 mmol) of sodium borohydride. After 30 min at room temperature, a further 40 mg (1.07 mmol) of sodium borohydride are added. After 30 min, the mixture is filtered over Celite. The filtrate is concentrated and then purified on a column of silica gel (eluent:EtOAc:PE 1:1). 65 mg of expected product are obtained in the form of a light-yellow solid.

Yield: 64%
m.p.=59°–60° C.
¹H NMR (CDCl₃): δ3.43 (t, 2H, J=7.1 Hz, CH₂), 3.82 (s, 3H, CH₃), 3.90 (s, 3H, CH₃), 4.63 (t, 2H, J=7.1 Hz, CH₂), 7.02 (s, 1H, H-2), 7.32 (d, 1H, $J_{4-6}$=2.9 Hz, H-4), 8.13 (d, 1H, $J_{6-4}$=2.9 Hz, H-6).

Stage J: 3-(2-aminoethyl)-5-methoxy-1-methylpyrrolo[2,3-b]pyridine

α) synthesis from the compound of Stage I 50 mg (2.12 10⁴ mmol) of the compound obtained in the above stage are dissolved in 1 cm³ of methanol. After addition of 10 mg of Raney nickel, the system is maintained under hydrogen pressure at 60° C. for 2.5 h. After cooling, the nickel is filtered off over Celite and rinsed with dichloromethane. The filtrate is concentrated and 40 mg of expected amine are obtained in the form of an oil. The product is used in the subsequent steps without purification.

Yield: 92%

IR (NaCl): ν=3300–3000 cm−1 ($NH_2$)

RMN ¹H (CDCl₃): δ1.56 (broad s, 2H, $NH_2$), 2.84 (t, 2H, J=6.7 Hz, $CH_2$), 3.00 (t, 2H, J=6.7 Hz, $CH_2$), 3.82 (s, 3H, $CH_3$), 3.89 (s, 3H, $CH_3$), 7.00 (s, 1H, H-2), 7.38 (d, 1H, $J_{4-6}$=2.8 Hz, H-4), 8.11 (d, 1H, $J_{6-4}$=2.8 Hz, H-6).

β) synthesis from the compound of Stage H

To 90 mg (2.36 mmol) of lithium aluminum hydride suspended in 2 cm³ of tetrahydrofuran are added 100 mg (4.29 10⁻⁴ mmol) of the compound obtained in Stage H in solution in 4 cm³ of tetrahydrofuran and 4 cm³ of dioxane. As soon as the addition is complete all of the starting material is consumed. The excess hydride is destroyed by gradual addition of 0.09 cm³ of water, 0.09 cm³ of 15% sodium hydroxide solution and 0.27cm³ of water. After 15 min, the precipitate is filtered off and washed with dichloromethane. The filtrate is concentrated and 70 mg of amine are obtained in the form of an oil, which product is used in the subsequent synthesis steps without purification.

Yield: 79%

PREPARATION 2: 3-(2-AMINOETHYL)-1H-PYRROLO[2,3-b]PYRIDINE

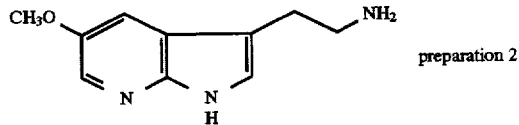

preparation 2

Stage A: 3-(2-nitrovinyl)-1H-pyrrolo[2,3-b]pyridine

Working as in Preparation 1, but starting from Stage H and using 3-formyl-1H-pyrrolo[2,3-b]pyridine (Verbiscar A. J., J. Med. Chem., 15, 1972, 149–152) as starting material.

Yield: 88% m.p.=decomposition>255° C.

IR (KBr): ν=3300–3000 cm⁻¹ (NH); ν=1615 cm⁻¹ ($NO_2$)

¹H NMR (DMSO-d₆): δ7.26 (dd, 1H, $J_{5-4}$=4.7 Hz, $J_{5-6}$=8.1 Hz, H-5), 8.07 (d, 1H, J=13.5 Hz, CH), 8.37 (d+s, 3H, J=13.5 Hz, CH+H-6+H-2), 8.49 (d, 1H, $J_{5-4}$=8.1 Hz, H-4), 12.7 (broad s, 1H, NH).

Stage B: 3-(2-nitroethyl)-1H-pyrrolo[2,3-b]pyridine

Yield: 61%

M.P.=145° C.

IR (KBr): ν=3300–2500 cm⁻¹ (NH); ν=1525 cm⁻¹ ($NO_2$)

¹H NMR (CDCl₃): δ3.49 (t, 1H, J=7.1 Hz, $CH_2$), 4.67 (t, 1H, J=7.1 Hz, $CH_2$), 7.13 (dd, 1H, $J_{5-4}$=7.8 Hz, $J_{5-6}$=4.6 Hz, H-5), 7.23 (s, 1H, H-2), 7.92 (dd, 1H, $J_{4-6}$=1.3 Hz, $J_{4-5}$=7.8 Hz, H-4), 8.35 (dd, 1H, $J_{6-4}$=1.3 Hz, $J_{6-5}$=4.6 Hz, H-6), 10.25 (broad s, 1H, NH).

Stage C: 3-(2-aminoethyl)-1H-pyrrolo[2,3-b]pyridine

Yield: quantitative

Oil

IR (NaCl): ν=3300–3000 cm⁻¹ ($NH_2$)

¹H NMR (DMSO-d₆): δ1.70 (broad s, 2H, $NH_2$), 2.69–2.84 (m, 4H, 2×$CH_2$), 7.00 (dd, 1H, $J_{5-4}$=7.8 Hz, $J_{5-6}$=4.7 Hz, H-5), 7.21 (s, 1H, H-2), 7.92 (dd, 1H, $J_{4-6}$=1.5 Hz, $J_{4-5}$=7.8 Hz, H-4), 8.16 (dd, 1H, $J_{6-4}$=1.5 Hz, $J_{6-5}$=4.7 Hz, H₆) 11.29 (broad s, 1H, NH).

PREPARATION 3: 3-(2-AMINOETHYL)-5-METHOXY-1H-PYRROLO[2,3-b]PYRIDINE

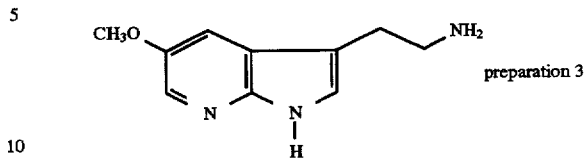

preparation 3

Stage A: 3,3,5-tribromo-2-oxo-1,3-dihydropyrrolo[2,3-b]pyridine

Bromine (54 cm³; 1.05 mol) is added dropwise, at room temperature, to a solution of 1H-pyrrolo[2,3-b]pyridine (10 g; 0.084 mol) in t-butanol (660 cm³) and water (660 cm³). After stirring for 19 h, the tert-butanol is evaporated off and the residual aqueous phase is basified with saturated aqueous sodium hydrogen carbonate solution. The desired product is recovered by filtration and, after drying under vacuum in the presence of phosphorus pentoxide, 26.7 g of the title compound are obtained as a brown solid.

Yield: 85% m.p.=157° C.

IR (KBr): ν=3300–3000 cm⁻¹ ($NH_2$), ν=1746 cm⁻¹ (C=O)

¹H NMR (CDCl₃): δ7.98 (d, 1H, $J_{4-6}$=2.7 Hz, H-4), 8.33 (d, 1H, $J_{6-4}$=2.7 Hz, H-6), 10.39 (s, 1H, NH)

Stage B: 5-bromo-2-oxo-1,3-dihydropyrrolo[2,3-b]pyridine

Zinc powder (8.8 g; 135 mmol) is added portionwise, under argon and at room temperature, to a solution of the compound obtained in the above stage (5 g; 13.5 mmol) in acetic acid (100 cm³). After vigorous stirring for 3 h, the reaction medium is hydrolyzed with water and extracted three times with ethylacetate. After drying over MgSO₄, the organic phase is evaporated and co-evaporated with toluene. The residual solid is purified by chromatography on silica gel (eluent:$CH_2Cl_2$:MeOH, 95:5), thereby allowing the title compound to be obtained in the form of an orange solid (2.2 g).

Yield: 76% m.p.=250° C.

IR (KBR): ν: 3300–3000 cm⁻¹ (NH), ν: 1728 cm⁻¹ (C=O)

¹H NMR (DMSO-d₆): δ4.10 (s, 2H, $CH_2$), 7.67 (d, 1H, $J_{4-6}$=2.3 Hz, H-4), 8.07 (d, 1H, $J_{6-4}$=2.3 Hz, H-6), 11.06 (s, 1H, NH).

Stage C: 5-bromo-1H-pyrrolo[2,3-b]pyridine

A 1.0M solution of borohydride-tetrahydrofuran complex in tetrahydrofuran (37.6 cm³; 37.6 mmol) is added dropwise under argon atmosphere and in an anhydrous medium, to the compound obtained in the above stage (2 g; 9.4 mmol) suspended in tetrahydrofuran (50 cm³) at 0° C. The reaction is stirred for 35 min at room temperature and is evaporated to dryness. The residue is taken up in aqueous 6N hydrochloric acid solution and heated until the solid has completely dissolved. After cooling, the solution is basified with aqueous 6N sodium hydroxide solution and extracted with ethyl acetate. The organic phase is dried over magnesium sulfate and evaporated. The residue is dissolved in acetic acid (20 cm³) and added, at room temperature, to a suspension of manganese (III) acetate dihydrate (4.1 g; 15.28 mmol) in acetic acid (20 cm³). After stirring for 45 min at 75° C., the solution is evaporated to dryness and co-evaporated with toluene; the residue is taken up in water and basified with saturated aqueous sodium hydrogen carbonate solution. After extraction with ethyl acetate (four times) the organic phases are dried over magnesium sulfate and evaporated. The residue obtained is purified by chromatography on silica gel (eluent::PE:EtOAc, 6:1 ) to give 920 mg of a slightly yellow solid.

Yield: 50%
m.p.=176° C.
IR (KBr): ν=3300–3000 cm$^{-1}$ (NH)
$^{1}$H NMR (CDCl$_{3}$): δ6.39 (d, 1H, J$_{3-2}$=2.9 Hz, H-3), 7.30 (d, 1H, J$_{2-3}$=2.9 Hz, H-2), 8.01 (d, 1H, J$_{4-6}$=2.2 Hz, H-4), 8.29 (d, 1H, J$_{6-4}$=2.2 Hz, H-6), 10.9 (s, 1H, NH).

Stage D: 5-methoxy -1H-pyrrolo[2,3-b]pyridine

A mixture of the compound obtained in the above stage (986 mg; 5.0 mmol), sodium methoxide (14.3 g; 265 mmol) and cuprous bromide (1.43 g; 10.01 mmol) is suspended in dimethylformamide (32 cm$^{3}$) and methanol (20 cm$^{3}$) and then heated at reflux for 2 h 30. After evaporation of the solvents, the residue is taken up in water and extracted with ethyl acetate; the aqueous phase is brought to neutral pH with aqueous 2N hydrochloric acid solution and extracted twice more with ethyl acetate. The organic phases are washed with water, dried over MgSO$_{4}$ and evaporated to give a solid which is purified by chromatography on silica gel (eluent: CH$_{2}$Cl$_{2}$/MeOH 99:1). The methoxylated product is obtained in the form of a slightly yellow solid (530 mg).

Yield: 72%
m.p.=162° C.
IR (KBr): ν=3300–3000 cm$^{-1}$ (NH)
$^{1}$H NMR (CDCl$_{3}$): δ3.83 (s, 3H, OCH$_{3}$), 6.38 (d, 1H, J$_{3-2}$=2.9 Hz, H-3), 7.28 (d, 1H, J$_{2-3}$=2.9 Hz, H-2), 7.41 (d, 1H, J$_{4-6}$=2.6 Hz, H-4), 8.06 (d, 1H, J$_{6-4}$=2.6 Hz, H-6), 10.26 (s, 1H, NH).

Stage E: 3-formyl-5-methoxy-1H-pyrrolo[2,3-b]pyridine

Phosphorus oxychloride (1.5 cm$^{3}$; 15.5 mmol) is added dropwise, under argon and in an anhydrous medium, to dimethylformamide (20 cm$^{3}$) maintained at 0° C. Ten minutes later, a solution of the compound obtained in the above stage (230 mg; 1.55 mmol) in dimethylformamide (5 cm$^{3}$) is added thereto using a cannula. The reaction is stirred for 30 min at 0° C. and then heated gradually to 80° C. After stirring for 2 h the reaction mixture is evaporated to dryness and taken up in water and the aqueous phase is basified with aqueous 50% sodium hydroxide and extracted with ethyl acetate. The organic phases are washed with water, dried over magnesium sulfate and evaporated and the residue is then purified by chromatography on silica gel (eluent:PE/EtOAc, 2:1, then 1:1 then 1:2). The title compound is obtained in the form of a yellow solid (113 mg).

Yield: 41%
m.p.: degradation above 191° C.
IR (KBr): ν=3300–3000 cm$^{-1}$ (NH), 1657 cm$^{-1}$ (C=O)
$^{1}$H NMR (DMSO-d$_{6}$): δ3.79 (s, 3H, OCH$_{3}$), 7.85 (d, 1H, J$_{4,6}$=3.0 Hz, H-4), 8.04 (d, 1H, J$_{6-4}$=3.0 Hz, H-6), 8.32 (s, 1H, H-2), 9.83 (s, 1H, CHO), 12.50 (s, 1H, NH).

Stage F: 5-methoxy-3-(2-nitrovinyl)-1H-pyrrolo[2,3-b]pyridine

The compound obtained in the above stage (260 mg; 1.48 mmol) in nitromethane (8 cm$^{3}$) is heated at 90° C. in the presence of ammonium acetate(285 mg; 3.7 mmol) for 3 h. After evaporation of the solvent, the nitrovinyl compound is obtained in the form of a yellow solid (166 mg).

Yield: 51%
m.p.=231° C.
IR (KBr): ν=3300–3000 cm$^{-1}$ (NH), ν=1500 cm$^{-1}$ (NO$_{2}$)
$^{1}$H NMR (DMSO-d$_{6}$): δ3.91 (s, 3H, OCH$_{3}$), 7.97 (d, 1H, J$_{4,6}$=2.7 Hz, H-4), 8.08 (d, 1H, J$_{6,4}$=2.7Hz, H-6), 8.14 (d, 1H, J=13.4Hz, CH), 8.30 (s, 1H, H-2), 8.37 (d, 1H, J=13.4 Hz, CH), 12.57 (s, 1H, NH).

Stage G: 5-methoxy-3-(2-nitroethyl)-1H-pyrrolo[2,3-b]pyridine

The nitrovinyl derivative obtained in the above stage (155 mg; 0.71 mmol) is suspended in isopropanol (14 cm$^{3}$) and chloroform (4.3 cm$^{3}$) in the presence of silica (355 mg), under argon and in an anhydrous medium. Sodium borohydride (140 mg; 3.55 mmol) is added portionwise. After stirring for 2 h at room temperature, the reaction is filtered over Celite and the solid residue is washed several times with chloroform and isopropyl alcohol. The product obtained after evaporation of the solvent is purified by chromatography on silica gel (eluent: CH$_{2}$Cl$_{2}$: MeOH 99:1 ); the title compound is obtained in the form of a white solid (90 mg).

Yield: 58%
m.p.=decomposition above 125° C.
IR (KBr): ν=3300–3000 cm$^{-1}$ (NH); ν=1540 cm$^{-1}$ (NO$_{2}$)
$^{1}$H NMR (DMSO-d$_{6}$): δ3.31 (t, 2H, J=7.1 Hz, CH$_{2}$), 3.81 (s, 3H, OCH$_{3}$), 4.82 (t, 2H, J=7.1 Hz, CH$_{2}$), 7.67 (s, 1H, H-2), 8.05 (d, 1H, J$_{4-6}$=2.8 Hz, H-4), 8.40 (d, 1H, J$_{6-4}$=2.8 Hz, H-6), 12.0 (s, 1H, NH).

Stage H: 3-(2-aminoethyl)-5-methoxy-1H-pyrrolo[2,3-b]pyridine

The compound obtained in the above stage (85 mg; 0.38 mmol) is stirred vigorously in methanol (2 cm$^{3}$) at 60° C. in the presence of Raney nickel under a hydrogen atmosphere for 22 h. The reaction is filtered over Celite; the solid residue is washed with methanol. After evaporation of the solvent, the residue (72 mg; 0.38 mmol) is suspended in dichloromethane (1 cm$^{3}$) under argon.

PREPARATION 4: 7-CHLORO-3-CYANOMETHYLFURO[2,3-c]PYRIDINE

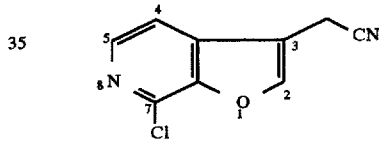

Stage A: 2-chloro-3-(oxiran-2-yl-methyloxy)pyridine

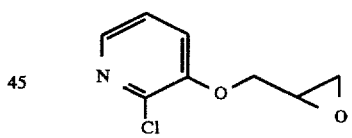

15 g (132 mmol) of 2-chloro-3-pyridinol are dissolved in 100 cm$^{3}$ of DMF and 6.34 g (158.6 mmol) of 60% sodium hydride (prewashed) are then added portionwise by spatula, at 0° C. The mixture is kept stirring at 45 min at room temperature under argon. 103.5 cm$^{3}$ (1.32 mmol) of epichlorohydrin in solution in 25 cm$^{3}$ of DMF are then added. Stirring is continued for 3 h at 60° C. After cooling to room temperature, the DMF is evaporated off and the mixture is hydrolyzed with 200 cm$^{3}$ of water and then extracted with CH$_{2}$Cl$_{2}$. The organic phase is dried over MgSO$_{4}$ and then evaporated. The epoxide is purified by chromatography on a column of silica (eluent:EtOAc:PE 7:3). 20.1 g of pure product are recovered in the form of a white solid.

Yield: 81%
m.p.=34°–36° C.
IR (KBr): ν=3030 cm$^{-1}$ (CH$_{2}$ epoxide), ν=1280 and 1200 cm$^{-1}$ (C—O—C)
$^{1}$H NMR (CDCl$_{3}$): δ2.78 (dd, 1H, J=2.9 Hz, J=4.6 Hz, Ar—O—CH$_{2}$—CH—CH$_{2}$); 2.88 (t, 1H, J=4.6 Hz, Ar—O—

CH$_2$—CH—CH$_2$), 3.32–3.36 (m, 1H, CH—CH$_2$), 4.00 (dd, 1H, J=5.9 Hz, J=11.4 Hz, Ar—O—CH$_2$—CH), 4.32 (dd, 1H, J=2.9 Hz, J=11.4 Hz, Ar—O—CH$_2$—CH), 7.14 (dd, 1H, J=4.4 Hz, J=8.1 Hz, H$_{pyr}$), 7.23 (d, 1H, J=8.1 Hz, H$_{pyr}$), 7.97 (d, 1H, J=4.4 Hz, H$_{pyr}$).

Stage B: 7-chloro-3-hydroxymethyl-2,3-dihydrofuro[2,3-c]pyridine

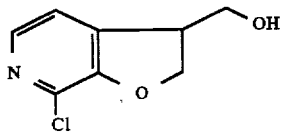

1 g (5.39 mmol) of the compound obtained in the above stage are dissolved in 10 cm$^3$ of tetrahydrofuran, followed by addition, at –78° C. over 15 min, of 5.4 cm$^3$ (10.8 mmol) of lithium diisopropylamide (2M) in solution in 8 cm$^3$ of THF. After stirring for 5 min, the mixture is hydrolyzed with 20 cm$^3$ of water at –78° C., and the mixture is then allowed to warm to room temperature. The THF is evaporated off. After extraction with CH$_2$Cl$_2$, the organic phase is dried over MgSO$_4$. Evaporation followed by chromatography on a column of silica (eluent:EtOAc:PE:3:1) leads to 0.7 g of the title compound in the form of a white solid.

Yield: 70% m.p.=110°–112° C.

IR (KBr): ν=3500–3000 cm$^{-1}$ (OH); ν=1215 cm-1 (C—O—C)

$^1$H NMR (CDCl$_3$): δ1.96 (t, 1H, J=4.1 Hz, OH), 3.72–3.81 (m, 1H, CH), 3.82–3.86 (m, 2H, CH$_2$—OH), 4.60 (dd, 1H, J=5.9 Hz, J=8.8 Hz, O—CH$_2$), 4.78 (t, 1H, J=8.8 Hz, O—CH$_2$), 7.17 (d, 1H, J=5.1 Hz, H$_{pyr}$), 7.93 (d, 1H, J=5.1 Hz, H$_{pyr}$).

MS m/z 186 (M+1).

Stage C: 7-chloro-3-tosyloxymethyl-2,3-dihydrofuro[2,3-c]pyridine

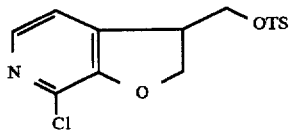

A solution of 1.54 g (8.08 mmol) of tosyl chloride, dissolved in 15 cm$^3$ of anhydrous CH$_2$Cl$_2$, is added, at 0° C., to a mixture of 1 g (5.39 mmol) of the compound obtained in the above stage dissolved in 25 cm$^3$ of CH$_2$Cl$_2$ and 2.25 cm$^3$ (16.2 mmol) of triethylamine. Stirring is continued at room temperature for 24 h. After evaporation under vacuum, the crude product is chromatographed on a column of silica (eluent:PE:EtOAc, 3:1). 1.72 g of pure product are thus isolated in the form of a white solid.

Yield: 94% m.p.=139°–140° C.

IR (KBr): ν=1634 and 1171 cm$^{-1}$ (O—SO$_2$)

$^1$H NMR (CDCl$_3$): δ2.45 (s, 3H, CH$_3$), 3.86–3.97 (m, 1H, CH), 4.09–4.21 (m, 2H, CH$_2$OTS), 4.44 (dd, 1H, J=9.9 Hz, J=6.0 Hz, O—CH$_2$), 4.71 (t, 1H, J=9.9 Hz, O—CH$_2$), 7.06 (d, 1H, J=4.9 Hz, H$_{pyr}$), 7.34 (d, 2H, J=8.2 Hz, H$_{arom}$), 7.71 (d, 2H, J=8.2 Hz, H$_{arom}$), 7.75 (d, 1H, J=4.9 Hz, H$_{pyr}$).

MS m/z 340 (M+1)

Stage D: 7-chloro-3-methylene-2,3-dihydrofuro[2,3-c]pyridine

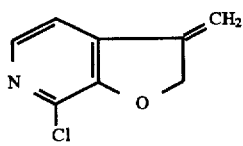

3 g (8.84 mmol) of the compound obtained in the above stage are dissolved in 30 cm$^3$ of acetonitrile, followed by addition, at room temperature, of 1.24 g (10.60 mmol) of 1,4-diazabicyclo[2.2.2]octane. Stirring is continued for 4 h at 80° C. under inert atmosphere. After evaporation under vacuum, the crude product is chromatographed on a column of silica (eluent:PE/EtOAc 1/1) to give 1.28 g of pure product in the form of a white solid.

Yield: 87% m.p.=98°–100° C.

IR (KBr): ν=1640 cm$^{-1}$ (C=CH$_2$)

$^1$H NMR (CDCl$_3$): δ5.24 (t, 2H, J=2.9 Hz, O—CH$_2$), 5.31 (m, 1H, =CH$_2$) 5.67 (m, 1H, CH$_2$), 7.24 (d, 1H, J=4.4 Hz, H$_{pyr}$), 7.99 (d, 1H, J=4.4 Hz, H$_{pyr}$).

Stage E: 3-bromomethyl-7-chlorofuro[2,3-c]pyridine

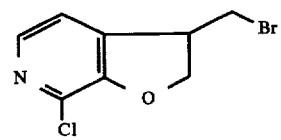

To 1 g (5.97 mmol) of the compound obtained in the above stage dissolved in 30 cm$^3$ of CCl$_4$ is added one spatulaful of 2,2'-azobisisobutyronitrile and 6.56 g (1.08 mmol) of N-bromosuccinimide. The reaction medium is heated at reflux using a 75 W lamp, under inert atmosphere, for 4 h. After cooling to room temperature, the solvent is evaporated off. The mixture is hydrolyzed with 50 cm$^3$ of water and is then extracted with CH$_2$Cl$_2$. The organic phase is dried over MgSO$_4$ and then evaporated. The crude product is purified by chromatography on a column of silica (eluent:PE:EtOAc, 8:2). 1.08 g of pure title compound are obtained in the form of a white solid.

Yield: 74% m.p.=105° C.

$^1$H NMR (CDCl$_3$): δ4.51 (s, 2H, CH$_2$), 7.55 (d, 1H, J=5.4 Hz, H$_{pyr}$), 7.80 (s, 1H, CH), 8.28 (d, 1H, J=5.4 Hz, H$_{pyr}$).

Stage F: 7-chloro-3-cyanomethylfuro[2,3-c]pyridine

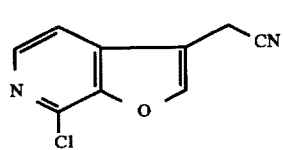

To 680 mg (2.77 mmol) of the compound obtained in the above stage, dissolved in 15 cm$^3$ of DMF, are added, at room temperature, 270 mg (4.15 mmol) of KCN. Stirring is continued for 5 hours. The DMF is evaporated off under vacuum and the crude product is purified by chromatography on a column of silica (eluent:PE:EtOAc 6:4). 477 mg of the title compound are obtained in the form of a white solid.

Yield: 90% m.p.=125° C.

IR (KBr): ν=2230 cm$^{-1}$ (CN)

$^1$H NMR (CDCl$_3$): δ3.69 (s, 2H, CH$_2$); 7.44 (d, 1H, J=5.2 Hz, H$_{pyr}$); 7.76 (s, 1H, CH); 8.20 (d, 1H, J=5.2 Hz, H$_{pyr}$).

PREPARATION 5: 3-(2-AMINOETHYL)-4-METHYL-1-PHENYLPYRROLO[2,3-c]PYRIDINE

PREPARATION 6: 3-(2-AMINOETHYL)-1H-PYRROLO[3,2-b]PYRIDINE
PREPARATION 7: 3-(2-AMINOETHYL)-1,4-DIMETHYLPYRROLO[2,3-b]PYRIDINE
PREPARATION 8: 3-(2-AMINOETHYL)-1,2-DIMETHYLPYRROLO[2,3-b]PYRIDINE
PREPARATION 9: 3-(2-AMINOBUTYL)-1-PHENYLPYRROLO[2,3-b]PYRIDINE
PREPARATION 10: 3-(2-AMINOETHYL)-5-METHOXY-1-METHYL-2-PHENYLPYRROLO[2,3-b]PYRIDINE
PREPARATION 11: 3-(2-AMINOETHYL)-2-PHENYLPYRROLO[2,3-b]PYRIDINE

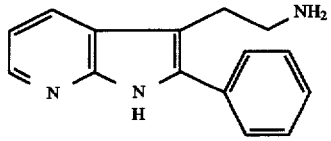

preparation 11

Stage A: 1-benzenesulfonylpyrrolo[2,3-b]pyridine

Crushed sodium hydroxide (5.3 g; 132 mmol) is suspended in dichloromethane (55 cm³) under argon and in an anhydrous medium, at 0° C.; benzyltriethylammonium chloride (250 mg; 1.1 mmol), and 7-azaindole (5g; 42.3 mmol) are successively added, followed by dropwise addition of benzenesulfonyl chloride (6.8 cm³; 52.9 mmol) in dichloromethane (17 cm³). After stirring for 15 min at 0° C. and then for 2 h at room temperature, the medium is filtered through a sinter funnel, the solid is washed with dichloromethane. After evaporation of the solvent, the residue is chromatographed on silica gel (eluent: petroleum ether: ethyl acetate 3:1) to give 10.7 g of white solid.

Yield: 98%
m.p.=134° C.
IR (KBr): v=1370 cm⁻¹ (SO₂), v=1175 cm⁻¹ (SO₂)
¹H NMR (CDCl₃): δ6.45 (d, 1H, J$_{3,2}$=2.8 Hz, H-3), 7.48–7.63 (unresolved multiplet, 5H aromatic, H-2, H-4), 7.11 (dd, 1H, J$_{5-6}$=4.4 Hz, J$_{5-4}$=8.0 Hz, H-5), 7.76 (d, 1H, J=7.4 Hz, aromatic), 8.15 (d, 1H, J=7.4 Hz, aromatic), 8.32 (d, 1H, J$_{6-5}$=4.4 Hz, H-6).

Stage B: 1-benzenesulfonyl-2-trimethylstannylpyrrolo[2,3-b]pyridine

The compound obtained in the above stage (5 g; 19.4 mmol) is dissolved in tetrahydrofuran (100 cm³) in the presence of N,N,N',N'-tetramethylethylenediamine (2.9 cm³; 19.4 mmol), under argon and in anhydrous medium; a 2M solution of lithium diisopropylamide is added at −22° C. to the above mixture. After stirring for 30 min at −22° C., tetramethyltin chloride (7.7 g; 38.7 mmol) in tetrahydrofuran (40 cm³) is added to the anion; the reaction is stirred for 30 min and water is then added. After extraction with dichloromethane (3 times), the organic phase is dried over magnesium sulfate and evaporated to give a solid which is purified on silica gel (eluent: petroleum ether: ethyl acetate 8:1); 6.15 g of white solid are obtained.

Yield: 76%
m.p.=139°–140° C.
IR (KBr): v=1364 cm⁻¹ (SO₂), v=1167 cm⁻¹ (SO₂)
¹H NMR (CDCl₃): δ0.49 (s, 9H, Sn(CH₃)₃), 6.73 (s, 1H, H-3), 7.10 (dd, 1H, J$_{5-6}$=4.4 Hz, J$_{5-4}$=8.1 Hz, H-5), 7.42–7.56 (m, 4H, 3 aromatic, H-4), 7.75, (d, 1H, J=7.35 Hz, aromatic), 8.12 (d, 1H, J=7.35 Hz, aromatic), 8.31 (d, 1H, J$_{6-5}$=4.4 Hz, H-6).

Stage C: 1-benzenesulfonyl-2-phenylpyrrolo[2,3-b]pyridine

A mixture of the compound obtained in the above stage (6.44 g; 15.3 mmol), iodobenzene (2cm³; 18.36 mmol), benzyltriethylammonium chloride (3.5 g; 15.3 mmol) and bis(triphenylphosphine)palladium (11) chloride (540 mg; 0.76 mmol) in acetonitrile (180 cm³) is heated at reflux for 44 h, under argon and in dry medium; after a further addition of bis(triphenylphosphine)palladium (11) chloride (540 mg; 0.76 mmol), the mixture is heated at reflux for 20 h. The reaction medium is evaporated to dryness; purification of the residue on silica gel (eluent: petroleum ether: ethyl acetate 5:1) allows 2.7 g of brown solid to be obtained.

Yield: 53%
m.p.=66° C.
IR (KBr): v=1399 cm⁻¹ (SO₂), v=1187 cm⁻¹ (SO₂)
¹H NMR (CDCl₃): δ6.50 (s, 1H, H-3), 7.16–7.56 (m, 10H, aromatic), 7.77 (dd, 1H, J=1.5 Hz, J$_{5-4}$=8.1 Hz, H-5), 7.87 (d, 1H, J$_{4-5}$=8.1 Hz, H-4), 8.47 (d, 1H, J=6.4 Hz, H-6)

Stage D: 3-formyl-2-phenyl-1-pyrrolo[2,3-b]pyridine

Phosphorus oxychloride (0.550 cm³; 5.86 mmol) is added dropwise, under argon, in anhydrous medium and at 0° C., to DMF (10 cm³); this mixture is stirred for 10 min at 0° C. and the compound obtained in the above stage (1.31 g; 3.9 mmol) in DMF (30 cm³) is added thereto. The medium is stirred for 30 min at 0° C. and then heated at 80° C. for 14 h; the reaction mixture is evaporated to dryness in the presence of toluene. The residue is taken up in water and brought to basic pH with 50% sodium hydroxide; the aqueous phase is extracted with ethyl acetate (4 times). The residues, which are insoluble in water and ethylacetate, are dissolved in 6M hydrochloric acid with heating; the acidic solution is basified with 50% sodium hydroxide and extracted with ethyl acetate (3 times). The combined organic phases are dried over magnesium sulfate and evaporated to give a solid which is purified by chromatography on silica gel (eluent: dichloromethane: methanol 99:1).

Yield: 76%
m.p.: higher than 250° C.
IR (KBr): v=3447 cm⁻¹ (NH), v=1667 cm⁻¹ (C=O)
¹H NMR (CDCl₃): δ7.30 (dd, 1H, J$_{5-6}$=5.2 Hz, J$_{5-4}$=7.7 Hz, H-5), 7.58–7.62 (m, 3H, aromatic), 7.80–7.83 (m, 2H, aromatic), 8.38 (d, 1H, J$_{6-5}$=5.2 Hz, H-6), 8.50 (d, 1H, J=8.6 Hz, H-4), 9.96 (s, 1H, CHO), 12.94 (s, 1H, H-1).

Stage E: 3-(2-nitrovinyl)-2-phenyl-1H-pyrrolo[2,3-b]pyridine

The compound obtained in the above stage (675 mg; 3.0 mmol) is dissolved in nitromethane (45 cm³) in the presence of ammonium acetate (705 mg; 9.1 mmol), under argon and in anhydrous medium. After refluxing for 20 h, the reaction is cooled to 0° C. and filtered through a sinter funnel; the yellow solid recovered is washed with dichloromethane and water. After drying, 593 mg of yellow solid are recovered.

Yield: 74%
m.p.=higher than 250° C.
IR (KBr): v=3431 cm⁻¹ (NH), v=1584 cm⁻¹ (NO₂), v=1315 cm⁻¹ (NO₂)
¹H NMR (DMSO-d₆): δ7.29–8.53 (series of unresolved multiplets, aromatic and vinylic, 10 H), 13.10 (s, 1H, H-1).

Stage F: 3-(2-nitroethyl)-2-phenyl-1H-pyrrolo[2,3-b]pyridine

The compound obtained in the above stage (585 mg; 2.2 mmol) is suspended in chloroform (46 cm³) and isopropanol (23 cm³) in the presence of 230–400 mesh silica (1.14 g) and sodium borohydride (210 mg; 5.5 mmol), under argon and in anhydrous medium. After stirring for 4 h at room temperature, acetic acid is added until the evolution of gas ceases; the mixture is filtered over Celite and the solid residue is washed with dichloromethane and methanol. After evaporation of the solvents and purification on silica gel (eluent:dichloromethane:methanol 99:1), 554 mg of white solid are obtained.

Yield: 94% m.p.=180° C.

IR (KBr): ν=3449 cm⁻¹ (NH), ν=1539 cm⁻¹ (NO₂)

¹H NMR (DMSO-d₆): δ3.52 (t, 2H, J=7.3 Hz, CH₂), 4.81 (t, 2H, J=7.3 Hz, CH₂—NO₂), 7.09 (dd, 1H, J=5.2 Hz, J=8.6 Hz, H-5), 7.41–7.66 (unresolved multiplet, 5 H aromatic), 8.07 (d, 1H, J=8.6 Hz, H-4), 8.23 (d, 1H, J=5.2 Hz, H-6), 11.92 (s, 1H, H-1).

Stage G: 3-(2-aminoethyl)-2-phenyl-1H-pyrrolo[2,3-b]pyridine

The compound obtained in the above stage (50 mg; 0.19 mmol) is stirred in acetic acid (5 cm³) in the presence of a catalytic amount of platinum oxide, under a hydrogen pressure of 55 psi. After stirring for 21 h at room temperature, filtration of the Celite and evaporation of the solvents, an oil is obtained which is used directly in the acetylation.

PREPARATION 12: 3-(2-AMINOETHYL)-5-BROMO-1H-PYRROLO[2,3-b]PYRIDINE

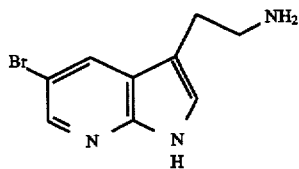

Stage A: 5-bromo-3-dimethylaminomethyl-1H-pyrrolo[2,3-b]pyridine

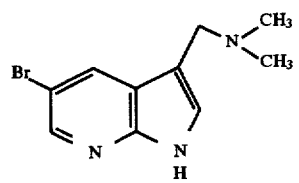

A mixture of 5-bromo-1H-pyrrolo[2,3-b]pyridine obtained in Stage C of Preparation 3 (1.0 g; 5.1 mmol), paraformaldehyde (330 mg) and dimethylammonium chloride (840 mg) in tert-butanol (30 cm³) is heated at reflux for 24 h. Further paraformaldehyde (110 mg) and dimethylammonium chloride (380 cm³) are added and the reaction medium is then stirred under reflux for 18 h. The reaction mixture is evaporated to dryness; the residue is taken up in water and concentrated hydrochloric acid is added to pH=1. The aqueous phase is washed 3 times with diethyl ether and the pH is then brought to 10 with 50% sodium hydroxide. After extraction of the aqueous phase with ethyl acetate (3 times) the organic phase is dried over magnesium sulfate and then evaporated. The oil obtained is then used directly in the following reaction.

Stage B: 3-(5-bromo-1H-pyrrolo [2,3-b]pyridinyl) methyltrimethylammonium iodide

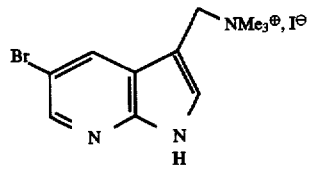

The compound obtained in the above stage (5.1 mmol, amount of 5-bromo-1H-pyrrolo [2,3-b]pyridine used) is taken up in acetone (20 cm³) and iodomethane (0.635 cm³; 10.2 mmol). A small amount of methanol is added to prevent agglomeration of the ammonium formed. The reaction mixture is stirred for 24 h at room temperature and then evaporated to dryness to give a white solid which is used in the following reaction.

Stage C: 5-bromo-3-cyanomethyl-1H-pyrrolo[2,3-b]pyridine

The compound obtained in the above stage is dissolved in dimethylformamide (25 cm³) in the presence of potassium cyanide (1.65 g; 25.5 mmol=5 equivalents relative to the amount of 5-bromo-1H-pyrrolo[2,3-b]pyridine). After stirring at room temperature for 24 h and then at 50° C. for 48 h, potassium cyanide (1.65 g; 25.5 mmol) is added and the reaction medium is stirred for a further 15 h, at 50° C. The reaction mixture is evaporated in the presence of toluene; the residue is taken up in ethyl acetate and washed with water (3 times) and then with brine (once). The organic phase is dried over magnesium sulfate and evaporated to give a solid. Purification on a column of silica (eluent: petroleum ether: ethyl acetate 2:1) allows 460 mg of white solid to be obtained.

Yield: 38% over 3 steps m.p.=169° C.

IR (KBr): ν=2260 cm⁻¹ (CN), ν=3132 cm⁻¹ (NH)

¹H NMR (DMSO-d₆): δ4.07 (s, 2H, CH₂—CN), 7.56 (s, 1H, H-2), 8.30 (s, 1H, H-4), 8.32 (s, 1H, H-6), 11.94 (s, 1H, H-1).

Stage D: 3-(2-aminoethyl)-5-bromo-1H-pyrrolo[2,3-b]pyridine

To the compound obtained in the above stage (100 mg; 0.42 mmol) in anhydrous tetrahydrofuran (5 cm³) under an argon atmosphere is added dropwise, at 0° C., a borane-tetrahydrofuran solution (1.26 cm³ of a 1.0M solution; 1.26 mmol). The reaction is stirred at reflux for 6 h and is then evaporated to dryness; the residue is taken up in 6M hydrochloric acid with heating until the precipitate has dissolved. After cooling the solution, 50% sodium hydroxide is added to pH=10; the aqueous phase is extracted with ethyl acetate (twice). After drying over magnesium sulfate, the organic phase is evaporated to give an oil which is used in the following reaction.

PREPARATION 13: 1-AMINOETHYLPYRROLO[2,3-b]PYRIDINE

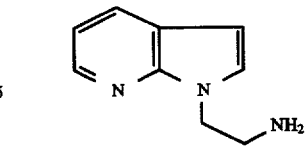

Stage A: 1-bromoethylpyrrolo[2,3-b]pyridine

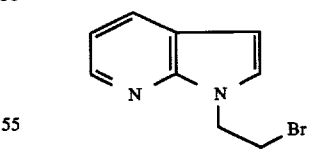

7-Azaindole (or pyrrolo[2,3-b]pyridine) (1 g; 8.47 mmol) is dissolved in N,N-dimethylformamide (DMF) (5 cm³) under an inert atmosphere. Sodium hydride (60% in oil) (0.51 g; 21.2 mmol) is added slowly to the reaction mixture. The medium is stirred for 1 h at room temperature. The preformed anion of 7-azaindole is added dropwise, using a pressure-equalized dropping funnel, to a solution of 1,2-dibromoethane (7.3 cm³; 84.7 mmol) in solution in DMF (4 cm³). After evaporation of the DMF, the residue is hydrolyzed with H₂O and then extracted with ethyl acetate; the organic phase is dried over MgSO$_4$. Evaporation of the solvent followed by purification on a column of silica (PE/EtOAc, 8:2) allows the title compound to be isolated in a yield of 67%, in the form of an oil.

$^1$H NMR (CDCl$_3$): δ(ppm): 3.76 (t, 2H, CH$_2$, J$_{CH2-CH2}$= 6.6 Hz), 4.68 (t, 2H, CH$_2$, J$_{CH2-CH2}$=6.6 Hz), 6.46 (d, 1H, H-3, J$_{3-2}$=2.7 Hz), 7.07 (dd, 1H, H-5, J$_{5-4}$=4.8 Hz, J$_{5-4}$=7.9 Hz), 7.27 (d, 1H, H-2, J$_{2-3}$=3.7 Hz), 7.91 (dd, 1H, H-4, J$_{4-5}$=7.9 Hz, J$_{4-6}$=1.5 Hz), 8.30 (dd, 1H, H-6, J$_{6-5}$=4.8 Hz, J$_{6-4}$=1.5 Hz).

Stage B: 1-azidoethylpyrrolo[2,3-b]pyridine

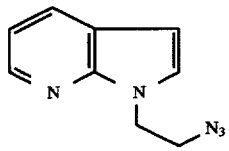

The compound obtained in the above stage (1.2 g; 5.33 mmol) dissolved in DMF (30 cm$^3$) is added to a solution of sodium azide (NaN$_3$) (1.04 g; 16 mmol) in DMF (30 cm$^3$) under inert atmosphere. The reaction medium is maintained at room temperature for 15 h. After evaporation of the solvent followed by hydrolysis (H$_2$O) and extraction with EtOAc, the organic phase is dried over MgSO$_4$ and then evaporated. The crude residue is purified on a column of silica (PE/EtOAc 8/2) to give the expected compound in the form of an oil, in a yield of 84%.

$^1$H NMR (CDCl$_3$): δ(ppm): 3.60 (t, 2H, CH$_2$, J$_{CH2-CH2}$= 5.2 Hz), 4.31 (t, 2H, CH$_2$, J$_{CH2-CH2}$=5.2 Hz), 4.31 (t, 2H, CH$_2$, J$_{CH2-CH2}$=5.2 Hz), 6.38 (d, 1H, H-3, J$_{3-2}$=3.3 Hz), 6.96 (dd, 1H, H-5, J$_{5-4}$=7.7 Hz, J$_{5-6}$=4.7 Hz), 7.13 (d, 1H, H-2, J$_{2-3}$=3.3 Hz), 7.8 (dd, 1H, H-4, J$_{4-5}$=7.7 Hz, J$_{4-6}$=1.5 Hz), 8.22 (dd, 1H, H-6, J$_{6-4}$=1.5 Hz, J$_{6-5}$=4.7 Hz).

Stage C: 1-aminoethylpyrrolo[2,3-b]pyridine

The compound obtained in the above stage (1.15 g; 6.14 mmol) is dissolved in ethanol (7 cm$^3$). Lindlar palladium (165 mg, 15% by weight) is added and the reaction medium is placed under a hydrogen atmosphere for 2 h at room temperature. After filtration over Celite followed by evaporation, the compound is obtained in the form of an oil, in quantitative yield.

$^1$H NMR (CDCl$_3$): δ(ppm): 3.17 (t, 2H, CH$_2$, J$_{CH2-CH2}$= 5.9 Hz), 4.3 (t, 2H, CH$_2$, J$_{CH2-CH2}$=5.9 Hz), 6.44 (d, 1H, H-3, J$_{3-2}$=3.3 Hz), 7.04 (dd, 1H, H-5, J$_{5-4}$=7.7 Hz, J$_{5-6}$=4.8 Hz), 7.23 (d, 1H, H-2, J$_{2-3}$=3.3 Hz), 7.89 (dd, 1H, H-4, J$_{4-5}$=7.7 Hz, J$_{4-6}$=1.5 Hz), 8.27 (dd, 1H, H-6, J$_{6-4}$=1.5 Hz, J$_{6-5}$=4.8 Hz).

PREPARATION 14: 3-CYANOMETHYL-5-METHOXYFURO[3,2-b]PYRIDINE

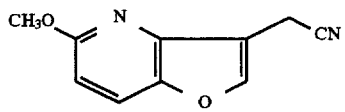

Stage A: 2-iodo-5-(oxiran-2-yl-methyloxy)pyridine

A solution of 1.84 g (8.33 mmol) of 5-hydroxy-2-iodopyridine in 18 cm$^3$ of DMF is cooled to 0° C. 220 mg (9.10 mmol) of sodium hydride is added in several portions. After 30 min at room temperature, 6.5 cm$^3$ (7.70 g; 53.26 mmol) of epichlorohydrin in solution in 3 cm$^3$ of DMF are added dropwise. The temperature is maintained at 60° C. for 2 h. The solvent is evaporated off. The residue is taken up in H$_2$O and extracted with CH$_2$Cl$_2$. After drying and concentrating the organic phase, the product is purified on a column of silica; eluent:ethyl acetate:petroleum ether 5:5.

2 g of an orange solid are obtained (m.p.=43°–44° C.). Yield: 84%

Stage B: (2,3-dihydro-5-iodofuro[3,2-b]pyrid-3-yl) methanol 1 g (3.01 mmol) of the compound obtained in the above stage in solution in 10 cm$^3$ of anhydrous tetrahydrofuran is cooled to -78° C. 3.01 cm$^3$ (7.22 mmol) of 2M lithium diisopropylamide diluted in 5 cm$^3$ of tetrahydrofuran are added dropwise. After 2 h at -78° C., the mixture is hydrolyzed with 20 cm$^3$ of water and extracted with CH$_2$Cl$_2$. After drying over MgSO$_4$ and concentration of the organic phase, the product is purified on a normal silica column:eluent:ethyl acetate:petroleum ether 2:1. 620 mg of a yellow solid are recovered (m.p.=120° C.). Yield=62%.

Stage C: 5-iodo-3-tosyloxymethylfuro[3,2-b]pyridine 1.85g (6.68.10$^{-3}$ mmol) of the compound obtained in the above stage in solution in 60 cm$^3$ of anhydrous dichloromethane are cooled to 0° C. 2.3 cm$^3$ (2.03 g; 20.03 mmol) of triethylamine are added dropwise followed by 1.91 g (10.01 mmol) of tosyl chloride in solution in 20 cm$^3$ of dichloromethane. After 30 h at room temperature, the solvent is evaporated off. The product is purified on a normal silica column; eluent:ethyl acetate:petroleum ether 1:3.

2.54 g of a white solid are recovered (m.p.: 138°–139° C.). Yield: 88%.

Stage D: 5-methoxy-3-methylfuro[3,2-b]pyridine

To 2.54 g (5.89 mmol) of compound obtained in the above stage in solution in 25 cm$^3$ of DMF are added 1.27 g (23.57 mmol) of sodium methoxide. After 1 h30 at 80° C., 320 mg (5.89 mmol; eq.) of sodium methoxide are added. After 3 h, the solvent is evaporated off and the residue is taken up in H$_2$O. The mixture is extracted with CH$_2$Cl$_2$. The organic phase is dried over MgSO$_4$. After evaporation of the solvent, the solvent is purified on a silica column; eluent:ethyl acetate:petroleum ether 1:3.

580 mg of a colorless oil are obtained. Yield=60%

Stage E: 3-bromomethyl-5-methoxyfuro[3,2-b]pyridine 350 mg (2.14 mmol) of compound obtained in the above stage in 7 cm$^3$ of anhydrous carbon tetrachloride, 400 mg (2.5 mmol) of NBS (N-bromosuccinimide) recrystallized from water and a spatula tipful of 2,2'-azobis-2-methylproprionitrile are heated at reflux for 9 h 30. The solvent is then evaporated off and the residue is purified on a column of silica; eluent:ethyl acetate:petroleum ether 5:95.

340 mg of an orange solid are obtained (m.p.: 86°–87° C.). Yield: 65%.

Stage F: 3-cyanomethyl-5-methoxyfuro[3,2-b]pyridine

To 340 mg (1.40 mmol) of compound obtained in the above stage in solution in 10 cm$^3$ of DMF are added 150 mg (2.25 mmol) of potassium cyanide. After 10 h at room temperature, the solvent is evaporated off. The residue is purified on a column of silica. Eluent:Ethyl acetate:petroleum ether 1:2.

220 mg of a white solid are obtained (m.p.: 95°–96° C.). Yield: 83%.

PREPARATION 15: 3-CYANOMETHYL-7-METHOXYFURO[2,3-c]PYRIDINE

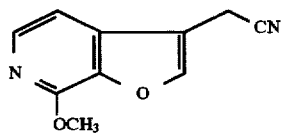

Stage A: 3-methyl-7-methoxy-2,3-dihydrofuro[2,3-c]pyridine

To 2.25 g (6.65 mmol) of the compound obtained in Stage C of Preparation 4 dissolved in 30 cm$^3$ of N,N- dimethylformamide, are added, at room temperature, 1.44 g (26.6 mmol) of sodium methoxide. Stirring is continued at 80° C. under inert atmosphere. After evaporation under vacuum, the crude product is extracted with $CH_2Cl_2$. The organic phase is dried over $MgSO_4$ and then evaporated under vacuum. The product is chromatographed on a column of silica (eluent:PE:EtOAc 6:4) to give 0.84 g of pure product in the form of a yellow oil.

Yield: 78%

MS m/z 164 (M+1)

$^1$H NMR ($CDCl_3$): δ2.18 (s, 3H, $CH_3$), 4.08 (s, 3H, O—$CH_3$), 7.03 (d, 1H, J=6 Hz, $H_{pyr}$), 7.87 (d, 1H, J=5.1 Hz, $H_{pyr}$).

Stage B: 3-bromomethyl-7-methoxyfuro[2,3-c]pyridine

To 0.840 g (5.15 mmol) of the compound obtained in the above stage dissolved in 15 $cm^3$ of $CCl_4$ are added a spatulaful of AIBN and 0.963 g (5.411 mmol) of N-bromosuccinimide. The reaction medium is heated at reflux using a 75 W lamp, under inert atmosphere, for 4 h. After cooling to room temperature, the solvent is evaporated off. The mixture is hydrolyzed with 30 $cm^3$ of water and then extracted with $CH_2Cl_2$. The organic phase is dried over $MgSO_4$ and then evaporated. The crude product is purified by chromatography on a column of silica (eluent:EP:EtOAc, 8:2). 0.573 g of the expected compound is recovered.

Yield: 46% m.p.: 110°–111° C.

IR (cm–1) (KBr): 1230 et 1210 (C—O—C—)

$^1$H NMR ($CDCl_3$) δ4.07 (s, 3H, O—$CH_3$), 4.51 (s, 2H, $CH_2$), 7.19 (d, 1H J=5.15 Hz, $H_{pyr}$), 7.69 (s, 1H, CH), 7.94 (d, 1H, J=5.15 $H_{pyr}$).

Stage C: 3-cyanomethyl-7-methoxyfuro[2,3-c]pyridine

To 360 mg (1.48 mmol) of the compound obtained in the above stage dissolved in 10 $cm^3$ of DMF are added, at room temperature, 155 mg (2.38 mmol) of KCN. Stirring is continued for 5 h. The DMF is evaporated off under vacuum and the crude product is then purified by chromatography on a column of silica (eluent:PE:EtOAc 6:4). 210 mg of the expected product are recovered in the form of a white solid.

Yield: 75%

IR (KBr): 2235 $cm^{-1}$ (CN)

$^1$H NMR ($CDCl_3$): δ3.72 (s, 2H, $CH_2$), 4.11 (s, 3H, O—$CH_3$), 7.12 (d, 1H, J=5.5 Hz, $H_{pyr}$), 7.72 (s, 1H, CH), 7.97 (d, 1H, J=5.5 Hz, $H_{pyr}$).

PREPARATION 16: 4-ACETAMIDO-1-TRIMETHYLSILYL-1-BUTYNE

Stage A: O-tosyl-3-butyn-1-ol

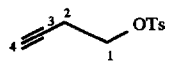

To a solution of 3-butyn-1-ol (0.540 $cm^3$; 7.13 mmol) and triethylamine (2 $cm^3$; 14.3 mmol) dans le dichloromethane (15 $cm^3$) is added, at 0° C., tosyl chloride (1.5 g; 7.85 mmol) in dichloromethane (10 $cm^3$). After stirring for 6 h at room temperature, the reaction is hydrolyzed with water and extracted with dichloromethane (twice). The organic phase is washed with water (3 times), dried over magnesium sulfate and evaporated. Purification on silica gel (eluent:petroleum ether:ethyl acetate 5:1) of the residue allows an oil to be obtained (1.37 g).

Yield: 86%

Stage B: O-tosyl-4-trimethylsilyl-3-butyn-1-ol

To a solution of the compound obtained in the above stage (6.45 g; 28.8 mmol) in tetrahydrofuran (130 $cm^3$), at –78° C., under argon and in anhydrous medium, is added dropwise a solution of 1.6M butyllithium in hexane (18.9 $cm^3$; 30.2 mmol). After stirring for 1 hour at –78° C., trimethylsilyl chloride (5.5 $cm^3$; 43.1 mmol) is added slowly. The reaction is stirred for 15 min at –78° C. and 1 h at room temperature and is then hydrolyzed with water. The medium is extracted with dichloromethane (twice) and dried over magnesium sulfate. After evaporation of the solvents, purification on silica gel (eluent:petroleum ether:ethyl acetate 95:5) of the residue allows 7.71 g of an oil to be obtained.

Yield: 90%

Stage C: 4-azido-1-trimethylsilyl-1-butyne

A mixture of the compound obtained in the above stage (5.45 g; 18.4 mmol) and sodium azide(3.6 g; 55.2 mmol) in dimethylformamide (25 $cm^3$) is stirred at room temperature, under argon and in dry medium, for 48 h. The medium is diluted in ethyl acetate and washed with water (5 times). After drying over magnesium sulfate, evaporation of the solvents allows an oil (3.08 g) to be obtained, which product is reduced directly.

Stage D: 4-amino-1-trimethylsilyl-1-butyne

A solution of the compound obtained in the above stage (1.96 g; 11.7 mmol) in diethyl ether (80 $cm^3$) is added dropwise to a suspension of lithium aluminum hydride (560 mg; 14.6 mmol) in diethyl ether (40 $cm^3$) under argon and in anhydrous medium. After stirring for 6 h at room temperature, the reaction is hydrolyzed with 0.570 $cm^3$ of water, 0.570 $cm^3$ of 15% sodium hydroxide and 1.71 $cm^3$ of water; the medium is filtered over Celite and the residue is washed with diethyl ether and 1,4-dioxane. Evaporation of the solvents allows an oil to be obtained, which product is acetylated directly.

Stage E: 4-acetamido-1-trimethylsilyl-1-butyne

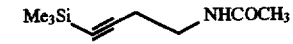

To the compound obtained in the above stage dissolved in dichloromethane (30 $cm^3$) and pyridine (2.6 $cm^3$) is added slowly, at 0° C. acetic anhydride (1.3 $cm^3$; 14.0 mmol), under argon and in dry medium. After stirring for 22 h at room temperature, the medium is hydrolyzed with water and extracted with dichloromethane. The organic phase is washed successively with water (5 times) and with brine (twice), dried over magnesium sulfate and evaporated. The oily residue is purified on silica gel (eluent:petroleum ether:ethyl acetate 2:1) to give 1.50 g of a white solid.

Yield: 70%, 3 steps m.p.=84° C.

IR (KBr): ν: 3268 $cm^{-1}$ (NH), ν: 1655 $cm^{-1}$ (C=O)

$^1$H NMR ($CDCl_3$): δ0.15 (s, 9H, Si ($CH_3)_3$), 1.99 (s, 3H, $COCH_3$), 2.43 (t, 2H, $J_{3-4}$=6.0 Hz, H-3), 3.38 (q, 2H, $J_{4-3}=J_{4-5}$=6.0 Hz, H-4), 5.76 (s, 1H, NH).

PREPARATION 17: 4-AMINO-3-IODOPYRIDINE

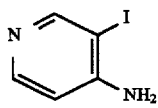

Stage A: 4-tert-butanamidopyridine

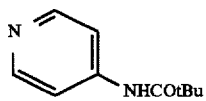

To a solution of 4-aminopyridine (1 g; 10.6 mmol) and triethylamine (1.9 cm$^3$; 13.25 mmol) in dichloromethane (15 cm$^3$) is added slowly, at 0° C., under argon and in dry medium, pivaloyl chloride (1.4 cm$^3$; 11.7 mmol) in dichloromethane (2 cm$^3$). The reaction is stirred for 10 min at 0° C. and then for 2 h at room temperature and is then diluted in dichloromethane and washed with water (twice). After drying over magnesium sulfate and evaporation of the solvents, the residue is purified on silica gel (eluent:dichloromethane:methanol 99:1) to give 1.7 g of white solid.

Yield: 91%
m.p.: 135° C.

Stage B: 3-iodo-4-tert-butanamidopyridine

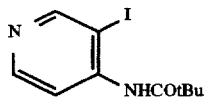

To a solution of the compound obtained in the above stage (4.4 g; 24.7 mmol) and tetramethylenediamine (8.9 cm$^3$; 59.25 mmol) in tetrahydrofuran (100 cm$^3$) is added dropwise, at −78° C., under argon and in dry medium, a 1.6M solution of butyllithium in hexane (37 cm$^3$; 59.25 mmol). After stirring for 1 h 30 at a temperature of between −20° C. and −10° C., a solution of iodine (9.4 g; 37.05 mmol) in THF (20 cm$^3$) is added to the reaction by transfer at −78° C. The medium is stirred for 10 min a −78° C. and for 30 min at room temperature, followed by addition of water; the medium is extracted with ethyl acetate (twice) and the organic phase is washed with saturated sodium thiosulfate solution and with water. After drying over magnesium sulfate and evaporation of the solvents, the residue is purified on silica gel (eluent:petroleum ether:ethyl acetate 1:1) to give 6.16 g of white solid.

Yield: 82%
m.p.: 158° C.

Stage C: 4-amino-3-iodopyridine

The compound obtained in the above stage (2.21 g; 7.3 mmol) in suspension in 10% sulfuric acid solution in water (73 cm$^3$) is stirred at reflux for 15 h. After cooling, the solution is basified with 50% sodium hydroxide and extracted with ethyl acetate (twice). After drying over magnesium sulfate and evaporation of the solvent, the residue is purified by chromatography on silica gel (eluent: dichloromethane: methanol 95:5) to give 1.54 g of white solid)

Yield: 97%
m.p.: 80°–81° C.
IR (KBr): ν: 3525 cm$^{-1}$ (NH$_2$)
$^1$H NMR (CDCl$_3$): δ4.69 (s, 2H, NH$_2$), 6.59 (d, 1H, J$_{5-6}$=5.15 Hz, H-5), 8.11 (d, 1H, J$_{6-5}$=5.15 Hz, H-6), 8.57 (s, 1H, H-2).

EXAMPLE 1

N-[2-(5-METHOXY-1-METHYLPYRROLO[2,3-b]PYRID-3-YL)ETHYL]ACETAMIDE

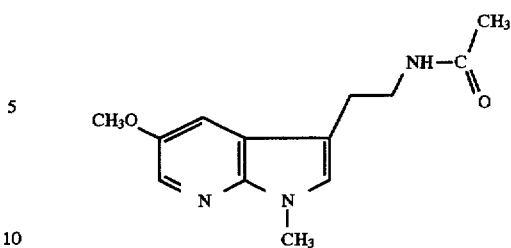

To 70 mg (3.42 10$^{-4}$ mmol) of the compound obtained in Preparation 1 in solution, at 0° C. in 0.7 cm$^3$ of anhydrous dichloromethane are added 0.08 cm$^3$ of pyridine and 0.04 cm$^3$ of acetic anhydride (4.09 10$^{-4}$ mmol; 42 mg). After 30 min at 0° C., the medium is hydrolyzed with 1 cm$^3$ of water, neutralized with saturated sodium bicarbonate solution and extracted with dichloromethane. After drying over magnesium sulfate, the organic phase is evaporated. The product is purified on a column of silica gel and obtained in the form of a solid (70 mg).

Yield: 83%
m.p.=115°–116° C.
IR (KBr): ν=3300 cm$^{-1}$ (NH), ν=1630 cm$^{-1}$ (C=O)
$^1$H NMR (CDCl$_3$): δ1.98 (s, 3H, CO—CH$_3$); 2.91 (t, 2H, J=6.8 Hz, CH$_2$), 3.56 (q, 2H, J=6.8 Hz, CH$_2$), 3.83 (s, 3H, CH$_3$), 3.91 (s, 3H, CH$_3$), 5.50 (broad s, 1H, NH), 6.99 (s, 1H, H-2), 7.38 (d, 1H, J$_{4-6}$=2.7 Hz, H-4), 8.12 (d, 1H, J$_{6-4}$=2.7 Hz, H-6).
MS m/z 248 (M+1)

EXAMPLE 2

N-[2-(1-H-PYRROLO[2,3-b]PYRID-3-YL)ETHYL]ACETAMIDE

Working as in Example 1, but starting with Preparation 2, the title compound is obtained.

Yield: 54%
m.p.=168° C.
$^1$H NMR (DMSO-d$_6$): δ1.75 (s, 3H, CH$_3$); 2.78 (t, 2H, J=7.2 Hz, CH$_2$), 3.29 (t, 2H, J=7.2 Hz, CH$_2$) 7.05 (dd, 1H, J$_{5-4}$=7.8 Hz, J$_{5-6}$=4.7 Hz, H-5), 7.22 (s, 1H, H-2), 7.95 (d, 1H, J$_{4-5}$=7.8 Hz, H-4), 8.13 (d, 1H, J$_{6-5}$=4.7 Hz, H-6).
MS m/z 204 (M+1)

EXAMPLE 3

N-[2-(5-METHOXY-1H-PYRROLO[2,3-b]PYRID-3-YL)ETHYL]ACETAMIDE

To a suspension of Preparation 3 in dichloromethane (1 cm$^3$) under argon, at 0° C., are added pyridine (86 cm$^3$) and then acetic anhydride (43 cm$^3$; 0.46 mmol) (the solution then becomes clear); the reaction is stirred for 2 h 30 min at 0° C. and for 1 h at room temperature (presence of a precipitate); the medium is hydrolyzed with water. The aqueous phase is extracted twice with dichloromethane and twice with ethyl acetate and the organic phases are washed with water. After drying over MgSO$_4$ and evaporation of the solvents, the residue is purified by chromatography on silica gel (eluent:CH$_2$Cl$_2$:MeOH 9:1). The title compound is obtained in the form of a slightly yellow solid (33 mg).

Yield: 37% for two steps
m.p.=159° C.
IR (KBR): ν=3300–3000 cm$^{-1}$ (NH), ν=1630 cm$^{-1}$ (CO)
$^1$H NMR (DMSO-d$_6$): δ1.73 (s, 3H, CO—CH$_3$); 2.81 (t, 2H, J=7.6 Hz, CH$_2$), 3.38 (q, 2H, J=7.6 Hz, CH$_2$), 3.93 (s, 3H, OCH₃), 7.63 (d, 1H, J$_{2,1}$=2.4 Hz, H-2), 7.95 (d, 1H, J$_{4,6}$=2.7 Hz, H-4), 8.37 (t, 1H, J=7.6 Hz, NH—CO), 8.40 (d, 1H, J$_{6,4}$=2.7 Hz, H-6), 11.9 (broad s, 1H, H-1)

MS (m/z): 234 (M+1)

EXAMPLE 4

N-[2-(7-CHLOROFURO[2,3-c]PYRID-3-YL)ETHYL] ACETAMIDE

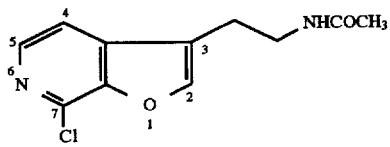

To 200 mg (1.04 mmol) of the compound obtained in Preparation 4 dissolved in 10 cm³ of acetic anhydride are added successively 31 mg (0.52 mmol) of Raney nickel and 125 mg (1.56 mmol) of sodium acetate. Stirring is continued for 12 h at 50° C. under a hydrogen atmosphere. After cooling to room temperature, the catalyst is filtered off on Celite. After evaporation to dryness, the product is hydrolyzed with 25 cm³ of water and extracted with CH₂Cl₂. The organic phase is dried over MgSO₄ and then evaporated under vacuum. The product is purified by chromatography on a column of silica (eluent:CH₂Cl₂:MeOH 95:5). 187 mg of pure product are recovered in the form of a solid.

Yield: 75% m.p.=104° C.

IR (KBr): ν=3310 cm⁻¹ (NH), ν=1660 cm⁻¹ (C=O)

¹H NMR (CDCl₃+D₂O): δ1.97 (s, 3H, CH₃), 2.92 (t, 2H, J=7.0 Hz, CH₂), 3.57 (t, 2H, J=7.0 Hz, CH₂), 7.48 (d, 1H, J=5.3 Hz, H$_{pyr}$), 7.66 (s, 1H, CH), 8.21 (d, 1H, J=5.3 Hz, H$_{pyr}$).

MS m/z 239 (M+1)

EXAMPLE 5

N-[2-(FURO[2,3-c]PYRID-3-YL)ETHYL]ACETAMIDE 200 mg (0.84 mmol) of the compound obtained in Example 4 are dissolved in 15 cm³ of acetic acid, followed by addition of 308 mg (4.7 mmol) of zinc. Stirring is continued at 60° C. for 5 h under an argon atmosphere. After cooling to room temperature, the catalyst is filtered off on cotton wool. After evaporation to dryness, the product is hydrolyzed with 5% NaHCO₃ and extracted with CH₂Cl₂. The organic phase is dried over MgSO₄ and then evaporated under vacuum. The product is purified by chromatography on a column of silica (eluent:CH₂Cl₂:MeOH, 95:5). 144 mg of pure product are recovered in the form of a solid.

Yield: 84% m.p. 90° C.

IR (KBr): ν=3290 cm⁻¹ (NH), ν=1660 cm⁻¹ (C=O)

¹H NMR (CDCl₃+D₂O): δ1.95 (s, 3H, CH₃), 2.91 (t, 2H, J=6.7 Hz, CH₂), 3.57 (t, 2H, J=6.7 Hz, CH₂), 7.52 (d, 1H, J=5.1 Hz, H$_{pyr}$), 7.58 (s, 1H, H$_{pyr}$), 8.42 (d, 1H, J=5.1 Hz, H$_{pyr}$), 8.85 (s, 1H, H$_{pyr}$).

MS m/z 205 (M+1)

EXAMPLES 6 TO 22

Working as in Example 1, but replacing the acetic anhydride with the appropriate acyl chloride or anhydride, the compounds of the following examples are obtained:

EXAMPLE 6

N-[2-(5-METHOXY-1-METHYLPYRROLO[2,3-b] PYRID-3-YL)ETHYL]PROPIONAMIDE

EXAMPLE 7

N-[2-(5-METHOXY-1-METHYLPYRROLO[2,3-b] PYRID-3-YL)ETHYL]BUTYRAMIDE

EXAMPLE 8

N-[2-(5-METHOXY-1-METHYLPYRROLO[2,3-b] PYRID-3-YL)ETHYL]PENTANAMIDE

EXAMPLE 9

N-[2-(5-METHOXY-1-METHYLPYRROLO[2,3-b] PYRID-3-YL)ETHYL]HEXANAMIDE

EXAMPLE 10

N-[2-(5-METHOXY-1-METHYLPYRROLO[2,3-b] PYRID-3-YL)ETHYL]2-IODOACETAMIDE

EXAMPLE 11

N-[2-(5-METHOXY-1-METHYLPYRROLO[2,3-b] PYRID-3-YL)ETHYL]TRIFLUOROACETAMIDE

EXAMPLE 12

N-[2-(5-METHOXY-1-METHYLPYRROLO[2,3-b] PYRID-3-YL)ETHYL]ISOPENTANAMIDE

EXAMPLE 13

N-[2-(5-METHOXY-1-METHYLPYRROLO[2,3-b] PYRID-3-YL)ETHYL] CYCLOPROPYLCARBOXAMIDE

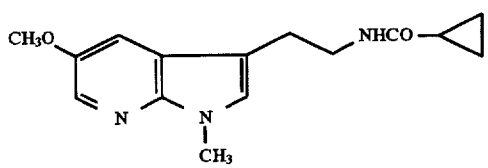

To 450 mg (2.19 mmol) of the compound of Preparation 1 in solution, at 0° C., in 9 cm³ of anhydrous dichloromethane are added 0.37 cm³ (2.63 mmol) of triethylamine and 0.24 cm³ (2.63 mmol) of cyclopropylcarbonyl chloride. After 1 h at 0° C., the medium is hydrolyzed with water, neutralized with saturated sodium bicarbonate solution and extracted with dichloromethane. After drying over magnesium sulfate, the organic phase is evaporated. The product is purified on a column of silica gel (eluent=ethyl acetate) and is obtained in the form of a yellow solid.

Yield: 77% m.p.: 133° C.

IR (KBr): ν=3233 cm⁻¹ (NH), ν=1639 cm⁻¹ (C=O).

¹H NMR (CDCl₃): δ0.64–0.70 (m, 2H, cyclopropyl), 0.91–0.97 (m, 2H, cyclopropyl), 1.18–1.26 (m, 1H, cyclopropyl), 2.88 (t, 2H, J=6.6 Hz, Ar—CH₂—), 3.54 (q, 2H, J=6.6 Hz, —CH₂—NH), 3.79 (s, 3H, N—CH₃), 3.85 (s, 3H, OCH₃), 5.65–5.78 (unresolved multiplet, 1H, NH), 6.97 (s, 1H, H-2), 7.35 (d, 1H, J=2.9 Hz, H-4), 8.08 (d, 1H, J=2.9 Hz, H-6).

MS m/z: 274 (M+1)

EXAMPLE 14

N-[2-(5-METHOXY-1-METHYLPYRROLO[2,3-b] PYRID-3-YL)ETHYL]CYCLOBUTYLCARBOXAMIDE

EXAMPLE 15

N-[2-(5-METHOXY-1-METHYLPYRROLO[2,3-b] PYRID-3-YL)ETHYL] CYCLOPENTYLCARBOXAMIDE

EXAMPLE 16

N-[2-(5-METHOXY-1-METHYLPYRROLO[2,3-b]PYRID-3-YL)ETHYL]CYCLOHEXYLCARBOXAMIDE

EXAMPLE 17

N-[2-(5-METHOXY-1-METHYLPYRROLO[2,3-b]PYRID-3-YL)ETHYL]CYCLOPROPYLMETHYLCARBOXAMIDE

EXAMPLE 18

N-[2-(5-METHOXY-1-METHYLPYRROLO[2,3-b]PYRID-3-YL)ETHYL]ALLYLCARBOXAMIDE

EXAMPLE 19

N-[2-(5-METHOXY-1-METHYLPYRROLO[2,3-b]PYRID-3-YL) ETHYL]ISOBUTYRAMIDE

EXAMPLE 20

N-[2-(5-METHOXY-1-METHYLPYRROLO[2,3-b]PYRID-3-YL)ETHYL]PROPENYLCARBOXAMIDE

EXAMPLE 21

N-[2-(5-METHOXY-1-METHYLPYRROLO[2,3-b]PYRID-3-YL)ETHYL]BROMOACETAMIDE

EXAMPLE 22

N-[2-(5-METHOXY-1-METHYLPYRROLO[2,3-b]PYRID-3-YL)ETHYL]HEPTANAMIDE

EXAMPLE 23

N-[2-(5-METHOXY-1-METHYLPYRROLO[2,3-b]PYRID-3-YL)ETHYL]FORMAMIDE

Working as in Example 1, but using formic acid instead of acetic anhydride, the title compound is obtained.

EXAMPLES 24 TO 32

Working as in Example 1, but replacing the acetic anhydride by the appropriate isothiocyanate or isocyanate, the compounds of the following examples are obtained:

EXAMPLE 24

N-[2-(5-METHOXY-1-METHYLPYRROLO[2,3-b]PYRID-3-YL)ETHYL]N'-METHYLUREA

EXAMPLE 25

N-[2-(5-METHOXY-1-METHYLPYRROLO[2,3-b]PYRID-3-YL)ETHYL]N'-ETHYLUREA

EXAMPLE 26

N-[2-(5-METHOXY-1-METHYLPYRROLO[2,3-b]PYRID-3-YL)ETHYL]N'-PROPYLUREA

To 470 mg (2.29 mmol) of the compound obtained in Preparation 1 in solution, at 0° C., in 5 cm³ of anhydrous dichloromethane are added 0.40 cm³ (2.75 mmol) of triethylamine and 0.26 cm³ (2.75 mmol) of propyl isocyanate. After 2 hours at 0° C., the medium is hydrolyzed with water, neutralized with saturated sodium bicarbonate solution and extracted with dichloromethane. After drying over magnesium sulfate, the organic phase is evaporated. The product is purified on a column of silica gel (eluent=ethyl acetate) and is obtained in the form of a yellow solid (490 mg).

Yield: 74% m.p.: 102°–103° C.

IR (KBr): $\nu$=3233 cm$^{-1}$ (NH), $\nu$=1625 cm$^{-1}$ (C=O).

$^1$H NMR (CDCl$_3$): δ0.88 (t, 3H, J=7.4 Hz, CH$_3$), 1.46 (sextuplet, 2H, J=7.4 Hz, CH$_2$—CH$_3$), 2.90 (t, 2H, J=6.6 Hz, Ar—CH$_2$), 3.07 (q, 2H, J=6.6 Hz, CH$_2$—NH—CO—), 3.48 (q, 2H, J=7.4 Hz, CO—NH—CH$_2$), 3.79 (s, 3H, N—CH$_3$), 3.88 (s, 3H, OCH$_3$), 4.20–4.29 (unresolved multiplet, 1H, NH), 4.31–4.40 (unresolved multiplet, 1H, NH), 6.97 (s, 1H, H-2), 7.37 (d, 1H, J=2.9 Hz, H-4), 8.09 (d, 1H, J=2.9 Hz, H-6).

MS m/z: 291 (M+1)

EXAMPLE 27

N-[2-(5-METHOXY-1-METHYLPYRROLO[2,3-b]PYRID-3-YL)ETHYL]N'-BUTYLUREA

EXAMPLE 28

N-[2-(5-METHOXY-1-METHYLPYRROLO[2,3-b]PYRID-3-YL)ETHYL]N'-METHYLTHIOUREA

EXAMPLE 29

N-[2-(5-METHOXY-1-METHYLPYRROLO[2,3-b]PYRID-3-YL)ETHYL]N'-ETHYLTHIOUREA

EXAMPLE 30

N-[2-(5-METHOXY-1-METHYLPYRROLO[2,3-b]PYRID-3-YL)ETHYL]N'-PROPYLTHIOUREA

EXAMPLE 31

N-[2-(5-METHOXY-1-METHYLPYRROLO[2,3-b]PYRID-3-YL)ETHYL]N'-BUTYLTHIOUREA

EXAMPLE 32

N-[2-(5-METHOXY-1-METHYLPYRROLO[2,3-b]PYRID-3-YL)ETHYL]N'-CYCLOPROPYLUREA

EXAMPLES 33 TO 38

Working as in Example 2, but using the appropriate reactants, the compounds of the following examples are obtained:

EXAMPLE 33

N-[2-(1-H-PYRROLO[2,3-b]PYRID-3-YL)ETHYL] PROPIONAMIDE

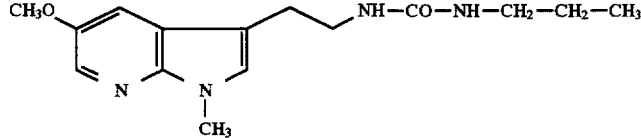

EXAMPLE 34

N-[2-(1-H-PYRROLO[2,3-b]PYRID-3-YL)ETHYL]
CYCLOPROPYLCARBOXAMIDE

EXAMPLE 35

N-[2-(1-H-PYRROLO[2,3-b]PYRID-3-YL)ETHYL]
CYCLOBUTYLCARBOXAMIDE

EXAMPLE 36

N-[2-(1-H-PYRROLO[2,3-b]PYRID-3-YL)ETHYL]
TRIFLUOROACETAMIDE

EXAMPLE 37

N-[2-(1-H-PYRROLO[2,3-b]PYRID-3-YL)ETHYL]N'-
METHYLUREA

EXAMPLE 38

N-[2-(1-H-PYRROLO[2,3-b]PYRID-3-YL)ETHYL]N'-
PROPYLUREA

EXAMPLES 39 TO 44

Working as in Example 3, but using the appropriate reactants, the compounds of the above examples are obtained:

EXAMPLE 39

N-[2-(5-METHOXY-1H-PYRROLO[2,3-b]PYRID-3-YL)
ETHYL]PROPIONAMIDE

EXAMPLE 40

N-[2-(5-METHOXY-1H-PYRROLO[2,3-b]PYRID-3-YL)
ETHYL]CYCLOPROPYLCARBOXAMIDE

EXAMPLE 41

N-[2-(5-METHOXY-1H-PYRROLO[2,3-b]PYRID-3-YL)
ETHYL]CYCLOBUTYLCARBOXAMIDE

EXAMPLE 42

N-[2-(5-METHOXY-1H-PYRROLO[2,3-b]PYRID-3-YL)
ETHYL]TRIFLUOROACETAMIDE

EXAMPLE 43

N-[2-(5-METHOXY-1H-PYRROLO[2,3-b]PYRID-3-YL)
ETHYL]N'-METHYLUREA

EXAMPLE 44

N-[2-(5-METHOXY-1H-PYRROLO[2,3-b]PYRID-3-YL)
ETHYL]N'-PROPYLUREA

EXAMPLES 45 TO 50

Working as in Example 4, but using the appropriate reactants, the compounds of the following examples am obtained:

EXAMPLE 45

N-[2-(7-CHLOROFURO[2,3-c]PYRID-3-YL)ETHYL]
PROPIONAMIDE

EXAMPLE 46

N-[2-(7-CHLOROFURO[2,3-c]PYRID-3-YL)ETHYL]
CYCLOPROPYLCARBOXAMIDE

EXAMPLE 47

N-[2-(7-CHLOROFURO[2,3-c]PYRID-3-YL)ETHYL]
CYCLOBUTYLCARBOXAMIDE

EXAMPLE 48

N-[2-(7-CHLOROFURO[2,3-c]PYRID-3-YL)ETHYL]
TRIFLUOROACETAMIDE

EXAMPLE 49

N-[2-(7-CHLOROFURO[2,3-c]PYRID-3-YL)ETHYL]N'-
METHYLUREA

EXAMPLE 50

N-[2-(7-CHLOROFURO[2,3-c]PYRID-3-YL)ETHYL]N'-
PROPYLUREA

EXAMPLES 51 TO 56

Working as in Example 5, but starting from Examples 45 to 50, the compounds of the following examples are obtained:

EXAMPLE 51

N-[2-(FURO[2,3-c]PYRID-3-YL)ETHYL]
PROPIONAMIDE

EXAMPLE 52

N-[2-(FURO[2,3-c]PYRID-3-YL)ETHYL]
CYCLOPROPYLCARBOXAMIDE

EXAMPLE 53

N-[2-(FURO[2,3-c]PYRID-3-YL)ETHYL]
CYCLOBUTYLCARBOXAMIDE

EXAMPLE 54

N-[2-(FURO[2,3-c]PYRID-3-YL)ETHYL]
TRIFLUOROACETAMIDE

EXAMPLE 55

N-[2-(FURO[2,3-c]PYRID-3-YL)ETHYL]N'-
METHYLUREA

EXAMPLE 56

N-[2-(FURO[2,3-c]PYRID-3-YL)ETHYL]N'-
PROPYLUREA

EXAMPLES 57 TO 62

Working as in Example 1, but starting with Preparations 5 to 10, the compounds of the following examples are obtained:

EXAMPLE 57

N-[2-(4-METHYL-1-PHENYLPYRROLO[2,3-c]PYRID-
3-YL)ETHYL]ACETAMIDE

EXAMPLE 58

N-[2-(1H-PYRROLO[3,2-b]PYRID-3-YL)ETHYL]
ACETAMIDE

EXAMPLE 59

N-[2-(1,4-DIMETHYLPYRROLO[2,3-b]PYRID-3-YL)
ETHYL]ACETAMIDE

EXAMPLE 60

N-[2-(1,2-DIMETHYLPYRROLO[2,3-b]PYRID-3-YL)ETHYL]ACETAMIDE

EXAMPLE 61

N-[2-(1-PHENYLPYRROLO[2,3-b]PYRID-3-YL)BUTYL]ACETAMIDE

EXAMPLE 62

N-[2-(5-METHOXY-1-METHYL-2-PHENYLPYRROLO[2,3-b]PYRID-3-YL)ETHYL]ACETAMIDE

EXAMPLES 63 TO 71

Using the synthetic methods described above, but with the appropriate reactants, the compounds of the following examples are obtained:

EXAMPLE 63

N-[2-(5-ETHOXY-1-METHYLPYRROLO[2,3-b]PYRID-3-YL)ETHYL]ACETAMIDE

EXAMPLE 64

N-[2-(5-PROPOXY-1-METHYLPYRROLO[2,3-b]PYRID-3-YL)ETHYL]ACETAMIDE

EXAMPLE 65

N-[2-(5-BUTYLOXY-1-METHYLPYRROLO[2,3-b]PYRID-3-YL)ETHYL]ACETAMIDE

EXAMPLE 66

N-[2-(5-ALLYLOXY-1-METHYLPYRROLO[2,3-b]PYRID-3-YL)ETHYL]ACETAMIDE

EXAMPLE 67

N-[2-(5-(BUT-2-ENYLOXY)-1-METHYLPYRROLO[2,3-b]PYRID-3-YL)ETHYL]ACETAMIDE

EXAMPLE 68

N-[2-(5-(PROP-2-ENYLOXY)-1-METHYLPYRROLO[2,3-b]PYRID-3-YL)ETHYL]ACETAMIDE

EXAMPLE 69

N-[2-(5-METHOXY-1-METHYL-2-ETHYLPYRROLO[2,3-b]PYRID-3-YL)ETHYL]ACETAMIDE

EXAMPLE 70

N-[2-(5-METHOXY-1-METHYL-2-BENZYLPYRROLO[2,3-b]PYRID-3-YL)ETHYL]ACETAMIDE

EXAMPLE 71

N-[2-(5-METHOXY-1-METHYL-2-(4-FLUOROBENZYL)PYRROLO[2,3-b]PYRID-3-YL)ETHYL]ACETAMIDE

EXAMPLE 72

N-[2.(2-PHENYL-1H-PYRROLO[2,3-b]PYRID-3-YL)ETHYL]ACETAMIDE

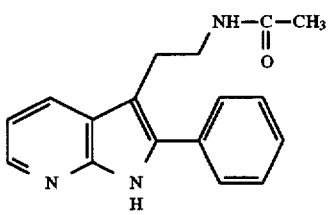

To Preparation 11 in dichloromethane (3 cm$^3$) and a few drops of 1,4-dioxane in the presence of pyridine (0.030 cm$^3$) is added slowly, at 0° C., under argon and in dry medium, acetic anhydride (0.015 cm$^3$; 0.15 mmol). After stirring for 3 hours at room temperature, the reaction mixture is hydrolyzed with water and extracted with ethyl acetate; the organic phase is washed with water (twice) and dried over magnesium sulfate. After evaporation of the solvents and purification on silica gel (eluents: dichloromethane: methanol 98:2), 30 mg of white solid are obtained.

Yield: 57% over 2 steps m.p.: 217° C.

IR (KBr): ν=3642 cm$^{-1}$ (NH), ν=1636 cm$^{-1}$ (C=O).

$^1$H NMR (DMSO-d$_6$): δ1.75 (s, 3H, CH$_3$), 2.95 (t, 2H, J=7.7 Hz, C$\underline{H}_2$—CH$_2$—NH) 3.31 (q, 2H, J=7.7 Hz, CH$_2$—NH), 7.07 (dd, 1H, J$_{5-6}$=5.4 Hz, J$_{5-4}$=8.7 Hz, H-5), 7.39 (m, 1H, aromatic), 7.50 (t, 2H, J=8.5 Hz, aromatic), 7.68 (d, 2H, J=8.5 Hz, aromatic), 7.96 (d, 1H, J$_{4-5}$=8.7 Hz, H-4), 7.98 (t, 1H, J=7.7 Hz, N$\underline{H}$—COCH$_3$), 8.21 (d, 1H, J$_{6-5}$=5.4 Hz, H-6), 11.75 (s, 1H, H-1).

MS m/z: 280 (M+1)

EXAMPLE 73

N-[2-(5-BROMO-1H-PYRROLO[2,3-b]PYRID-3-YL)ETHYL]ACETAMIDE

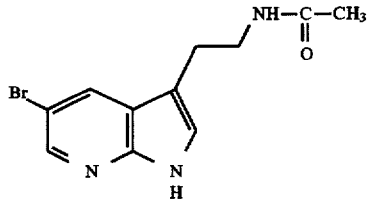

To a suspension of the compound obtained in Preparation 12 in dichloromethane (5 cm$^3$) and a few drops of 1,4-dioxane, under argon and at 0° C., are added pyridine (0.064 cm$^3$) and acetic anhydride (0.032 cm$^3$; 0.34 mmol); the reaction mixture is stirred for 2 h at room temperature. The medium is hydrolyzed with water and extracted with ethyl acetate (twice). After drying over magnesium sulfate and evaporation of the solvents, the residue is purified by chromatography on silica gel (eluent: dichloromethane:methanol 98:2) to give a white solid (60 mg).

Yield: 51% over two steps m.p.: 209° C.

IR (KBr): ν=3264 and 3151 cm$^{-1}$ (NH), ν=1643 cm$^{-1}$ (C=O).

$^1$H NMR (DMSO-d$_6$): δ1.77 (s, 3H, COCH$_3$), 2.77 (t, 2H, J=7.4 Hz, CH$_2$), 3.28 (q, 2H, J=7.4 Hz, C$\underline{H}_2$—NH), 7.33 (s, 1H, H-2), 7.88 (t, 1H, J=7.4 Hz, N$\underline{H}$—CO—), 8.16 (d, 1H, J=2.6 Hz, H-4), 8.22 (d, 1H, J=2.6 Hz, H-6), 11.59 (s, 1H, H-1).

MS m/z: 283 (M+1)

EXAMPLE 74

N-[2-(PYRROLO[2,3-b]PYRID-1-YL)-ETHYL] ACETAMIDE

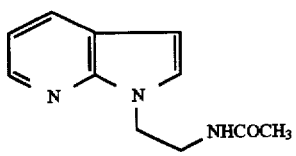

The compound obtained in Preparation 13 (500 mg; 310 mmol) is dissolved in 6 cm³ of dichlormmethane. 0.752 cm³ of pyridine and 0.879 cm³ of acetic anhydride in ice are added. The mixture is left stirring for 2 h. It is hydrolyzed with water and extracted with dichloromethane. Dichloromethane is incorporated and the pyridine is evaporated off with toluene. The product is purified on a column of silica (eluent CH₂Cl₂//CH₂Cl₂/MeOH 5%) and then recrystallized from cyclohexane.

Yield: 73% m.p.: 85° C.

¹H NMR (CDCl₃): δ2.15 (s, 3H, COC$\underline{H}_3$), 3.65–3.75 (m, 2H, C$\underline{H}_2$—NH), 4.41–4.50 (m, 2H, N—C$\underline{H}_2$), 6.50 (d, 1H, H₃), 6.72–6.80 (m, 1H, N—$\underline{H}$), 7.12 (dd, 1H, H₅ arom), 7.22 (d, 1H, H₂), 7.98 (d, 1H, H₄), 8.32 (d, 1H, H₆)

MS m/z: 204 (M+1)

IR: ν=3302 cm⁻¹ (NH), ν=1635 cm⁻¹ (C=O).

EXAMPLE 75

N-[2-(5-METHOXYFURO[3,2-b]PYRID-3-YL)ETHYL] ACETAMIDE

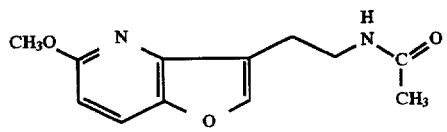

To 310 mg (1.65 mmol) of the compound of Preparation 14 in solution in 25 cm³ of acetic anhydride are added 43 mg (8.24.10⁻⁴ mmol) of Raney nickel prewashed in ethanol and then in acetic anhyddde, followed by 203 mg (2.47 mmol) of sodium acetate. Stirring is continued under a hydrogen atmosphere for 4 h 45 at 50° C. and the solvent is then evaporated off. The residue is taken up in H₂O and extracted with CH₂Cl₂. After drying over MgSO₄, the organic phase is concentrated. The product is purified on a column of silica, eluting with ethyl acetate. 290 mg of a white solid (m.p.=85° C.) are obtained, which product is recrystallized from cyclohexane.

Yield: 75%

IR: 3312 cm⁻¹ (NH); 1632 cm⁻¹ (C=O); 1620 cm⁻¹ (C=O)

¹H NMR (CDCl₃): 2.01 (s, 3H, C$\underline{H}_3$), 2.94 (t, 2H, C$\underline{H}_2$—CH₂—NH), 3.02 (q, 2H, CH₂—C$\underline{H}_2$—NH), 4.19 (s, 3H, C$\underline{H}_3$—O), 5.35–5.55 (unresolved multiplet, 1H, NH), 7.18 (d, 1H, J=5.5 Hz, H₂), 7.99 (d, 1H, J=5.5 Hz, H₃).

MS m/z: 235 (M+1)

EXAMPLES 76 TO 80

Working in a similar manner, but using the appropriate reactants for the procedures described in the above examples, the compounds of the following examples are obtained.

EXAMPLE 76

N-[2-(7-METHOXYFURO[2,3-c]PYRID-3-YL)-ETHYL] ACETAMIDE

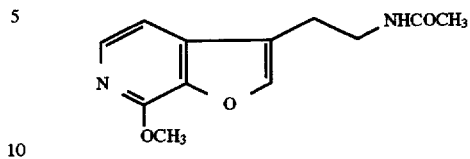

To 176 mg (0.935 mmol) of the compound obtained in Preparation 15 dissolved in 10 cm³ of acetic anhydride are successively added 27 mg (0.467 mmol) of Raney nickel and 115 mg (1.4 mmol) of sodium acetate. Stirring is continued for 4 h at 50° C. under a hydrogen atmosphere. After cooling to room temperature, the catalyst is filtered off on Celite. After evaporation to dryness, the product is hydrolyzed with 25 cm³ of water and extracted with CH₂Cl₂. The organic phase is dried over MgSO₄ and then evaporated under vacuum. The product is purified by chromatography on a column of silica (eluent:CH₂Cl₂:MeOH 95:5). 176 mg of product are recovered in the form of a solid.

Yield: 82% m.p.: 99°–100° C.

IR (KBr): 3030 cm⁻¹ (NH); 1610 cm⁻¹ (C=O); 1080 cm⁻¹ (C—O—C)

¹H NMR (CDCl₃+D₂O): δ1.89 (s, 3H, CH₃), 2.83 (t, 2H, J=6.6 Hz, CH₂), 3.50 (t, 2H, J=6.6 Hz, CH₂), 4.07 (s, 3H, O—CH₃), 7.06 (d, 1H, J=5.5 Hz, H_{pyr}), 7.48 (s, 1H, CH), 7.87 (d, 1H, J=5.5 Hz, H_{pyr}).

EXAMPLE 77

N-[2-(5-METHOXY-2-PHENYLPYRROLO[2,3-b] PYRID-3-YL)ETHYL]ACETAMIDE

EXAMPLE 78

N-[2-(2-TRIMETHYLSILYLPYRROLO[3,2-c]PYRID-3-YL)]ACETAMIDE

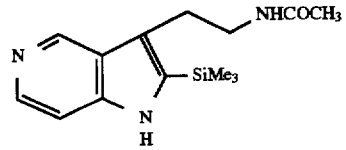

The compounds of Preparations 16 (200 mg; 0.91 mmol) and 17 (334 mg; 1.82 mmol) in the presence of triethylamine (0.380 cm³; 2.7 mmol) and bis(triphenylphosphine) palladium (II) chloride (64 mg; 0.091 mmol) in hexamethylphosphotriamide (4 cm³) are stirred at 100° C. for 15 h, under argon and in anhydrous medium; since the reaction has made little progress, 64 mg of bis(triphenylphosphine) palladium (II) chloride and 0.380 cm³ of triethylamine are added to the medium. The reaction is stirred for 22 h at 100° C. and then diluted in ethyl acetate and methanol; the organic phase is washed with water (6 times), dried over magnesium sulfate and evaporated. Purification of the residue on silica gel (eluent:dichloromethane:methanol 85:15) allows 75 mg of beige solid to be obtained.

Yield: 30% m.p.: decomposition above 75° C.

IR (KBr): ν: 3253 cm⁻¹ (NH); ν: 1653 cm⁻¹ (C=O)

¹H NMR (DMSO-d₆): δ0.37 (s, 9H, Si(C$\underline{H}_3$)₃), 1.79 (s, 3H, COC$\underline{H}_3$), 2.94 (t, 2H, J=6.6 Hz, C$\underline{H}_2$—N), 3.23 (q, 2H, J=6.6 Hz, Ar—$CH_2$), 7.40 (d, 1H, $J_{7-6}$=5.8 Hz, H-7), 8.03 (t, 1H, J=6.6 Hz, N$\underline{H}$—CO), 8.15 (d, 1H, $J_{6-7}$=5.8 Hz, H-6), 8.90 (s, 1H, H-4), 11.20 (s, 1H, H-1).

MS m/z: 276 (M+1)

EXAMPLE 79

N-[2-(5-PHENYLPYRROLO[3,2-b]PYRID-3-YL) ETHYL]ACETAMIDE

F: 181° C.

EXAMPLE 80

N-[2-(5-METHOXYTHIENO[3,2-b]PYRID-3-YL) ETHYL]ACETAMIDE

PHARMACOLOGICAL STUDY

EXAMPLE A

STUDY OF THE ACUTE TOXICITY

The acute toxicity was assessed after oral administration to groups of 8 mice (26±2 grams). The animals were observed at regular intervals throughout the first day and daily for the two weeks following the treatment. The $LD_{50}$ leading to the death of 50% of the animals was evaluated.

The $LD_{50}$ of the test products is greater than 1 000 mg.kg$^{-1}$ for most of the compounds studied, thereby indicating the low toxicity of the compounds of the invention.

EXAMPLE B

STUDY OF THE BINDING TO THE MELATONIN RECEPTORS

B1) Study on sheep pars tuberails cells

The studies of the binding of the compounds of the invention to the melatonin receptors were performed according to the standard techniques, on sheep pars tuberails cells. The pars tuberails of the adenohypophysis is in effect characterized, in mammals, by a high density of melatonin receptors (Journal of Neuroendocrinology 1989, vol. (1), pp 1–4).

PROCEDURE

1) Sheep pars tuberails membranes are prepared and used as target tissue in saturation experiments in order to determine the binding capacities and affinities for 2-[$^{125}$I]-iodomelatonin.

2) The sheep pars tuberails membranes are used as target tissue, with the vadous test compounds, in experiments of competitive binding relative to 2-iodomelatonin.

Each experiment is performed in triplicate and a range of different concentrations is tested for each compound.

The results make it possible to determine, after statistical treatment, the binding affinities of the test compound.

RESULTS

It is seen that the compounds of the invention possess a powerful affinity for the melatonin receptors, this affinity being stronger than that for melatonin itself.

B2) Study on chick (Gallus domesticus) brain cell membranes

The animals used are 12-day-old chicks (Gallus domesticus). They are sacrificed between 13.00 h and 17.00 h on the day of their arrival. The brains are rapidly removed and frozen at −200° C. and then stored at −80° C. The membranes are prepared according to the method described by Yuan and Pang (Journal of Endocrinology 1991, 128, pp 475–482). 2-[$^{125}$I]-iodomelatonin is incubated in the presence of the membranes in a solution buffered to pH 7.4 for 60 min at 25° C. After this period, the membrane suspension is filtered (Whatman GF/C). The radioactivity retained on the filter is determined using a Beckman® LS 6000 liquid scintillation counter.

The products used are:

2-[$^{125}$I]-iodomelatonin melatonin common products test compounds

In primary screening, the molecules are tested at 2 concentrations ($10^{-7}$ and $10^{-5}$M). Each result is the avemge of n=3 independent measurements. The test compounds are also subjected to a quantitative determination of their efficacy ($IC_{50}$) They are used at 10 different concentrations.

Thus, the $IC_{50}$ values found for the preferred compounds of the invention, which correspond to the values of the affinity, show that the binding of the test compounds is very powerful.

EXAMPLE C

FOUR-PLATE TEST

The products of the invention are administered esophageally to groups of ten mice. One group receives gum syrup. 30 min after administration of the products to be studied, the animals are placed in chambers the floor of which comprises four metal plates. Each time the animal passes from one plate to another, it receives a mild electric discharge (0.35 mA). The number of passages is recorded for one minute. After administration, the compounds of the invention significantly increase the number of passages, which shows the anxiolytic activity of the derivatives of the invention.

EXAMPLE D

COMPOUNDS OF THE INVENTION ON THE CIRCADIAN RHYTHMS OF RAT LOCOMOTOR ACTIVITY

The involvement of melatonin in driving, via the alternating day/night cycle, most of the physiological, biochemical and behavoral circadian rhythms has made it possible to establish a pharmacological model for the search for melatoninergic ligands.

The effects of the molecules are tested on a number of parameters and in particular on the circadian rhythms of locomotor activity, which represent a reliable marker of the activity of the endogenous circadian clock.

In this study, the effects of such molecules on a particular experimental method, namely a rat placed in temporal isolation (permanent darkness), is evaluated.

EXPERIMENTAL PROCEDURE

On their arrival at the laboratory, one-month-old male Long Evans rats are subjected to a lighting cycle of 12 h of light per 24 h (12:12 LD).

After 2 to 3 weeks of adaptation, they are placed in cages equipped with a wheel connected to a recording system so as to detect the phases of locomotor activity and thus to monitor the nyctohemeral (LD) or circadian (DD) rhythms.

As soon as the rhythms recorded show evidence of being stably driven by the 12:12 LD lighting cycle, the rats are placed in permanent darkness (DD).

Two to three weeks later, when the free, non-driven pattern (rhythm reflecting that of the endogenous clock) is cleady established, the rats receive a daily administration of the test molecule.

The observations are made by virtue of the visualization of the rhythms of activity:

rhythms of activity driven by the lighting rhythm, disappearance of the driving pattern for the rhythms in permanent darkness, rhythms driven by the daily administration of the molecule; transient or long-lasting effect.

A software program makes it possible:

to measure the duration and intensity of the activity, the period of the rhythm in the animals under free, non-driven conditions and during the treatment, possibly to demonstrate, by spectral analysis, the existence of circadian and non-circadian components.

RESULTS

It is clearly seen that the compounds of the invention make it possible to have a powerful effect on the circadian rhythm via the melatoninergic system.

EXAMPLE E

ACTIVITY OF THE PRODUCTS OF THE INVENTION ON ISCHEMIC MICROCIRCULATION

The experimental study was performed on the cremaster muscles of male rats (Sprague-Dawley) after ligature of the common lilac artery.

The muscles were placed in a transparent chamber, infused with a solution of bicarbonate buffer equilibrated with a 5/95% $CO_2/N_2$ gas mixture. The speed of the red blood cells and the diameter of the arterioles of first or second order irrigating the chromaster were measured, and the arteriolar blood flow was calculated. Identical information was obtained for four types of venule.

the same type of measurement was made simultaneously:

on the cremaster infused normally, on the cremaster under ligature, that is to say the cremaster under ischemia 2, 7, 14 and 21 days after ligature.

Two groups of animals were studied:

a control group without treatment, a group treated orally with a product of the invention, at an amount of 0.1 mg.kg$^{-1}$ per day.

No difference in the speed of the red blood cells or in the diameter of the vessels in the cremaster muscles irrigated normally was observed in the treated animals relative to the controls.

On the other hand, in the cremaster muscle under ischemia, the average diameter of the arterioles was improved in the treated animals relative to the controls. The speed of the red blood cells was normalized by a 21-day treatment.

In point of fact, in the treated animals, the speed of the red blood cells and the blood flow measured 7 days after the ligature showed no significant difference with the values obtained in the non-ischemic cremaster. These results are obtained without modification of the arterial pressure.

These results indicate that chronic treatment with a compound of the invention improves the microcirculation and the blood irrigation in areas under ischemia.

EXAMPLE F

STIMULATION OF THE IMMUNE RESPONSES

Sheep red blood cells were administered to groups of six mice. These groups of mice were then treated subcutaneously with the compounds of the invention for six days and a control group was treated with a placebo. The mice were then left alone for four weeks, after which time they received a repeat injection of sheep red blood cells without receiving new administrations of product of the invention. The immune response was evaluated 3 days after the repeat injection. It is statistically higher in the group treated with the compounds of the invention.

EXAMPLE G

ANTIARRYTHMIC ACTIVITY

PROCEDURE (Ref: LAWSON J. W. et al. J. Pharmacol. Exper. Therap. 1968, 160, pp 22–31)

The test substance is administered intraperitoneally to a group of 3 mice 30 min before exposure to anesthesia by chloroform. The animals are then observed for 15 min. The absence of recording of arrythmia and of heart rates above 200 beats/min (control: 400–480 beats/min) in at least two animals indicates significant protection.

EXAMPLE H

PHARMACEUTICAL COMPOSITION: TABLETS 1000 tablets containing 5 mg dose of N-[2-(5-methoxy-1-methylpyrrolo[2,3-b]pyrid-3-yl)ethyl]acetamide

| | |
|---|---|
| N-[2-(5-Methoxy-1-methylpyrrolo[2,3-b]pyrid-3-yl)ethyl]-acetamide | 5 g |
| Wheat starch | 20 g |
| Corn starch | 20 g |
| Lactose | 30 g |
| Magnesium stearate | 2 g |
| Silica | 1 g |
| Hydroxypropylcellulose | 2 g |

We claim:

1. A compound selected from those of formula (I):

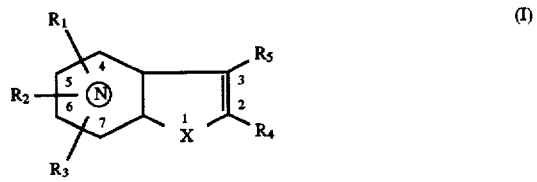

in which $R_1$, $R_2$, $R_3$ and $R_4$ represent, independently of each other, hydrogen or a radical being chosen from halogen, hydroxyl, Ra, and —O—Ra; with Ra chosen from alkyl, alkyl substituted with one or more halogens, trialkylsilyl, alkenyl, alkynyl, cycloalkyl, cycloalkylalkyl, aryl, substituted aryl, arylalkyl, and substituted arylalkyl;

$R_5$ represents a group of formula —A—B—Y in which A represents a ($C_1$-$C_6$) alkylene chain which is unsubstituted or substituted with one or more alkyls, B represents a group $B_1$, $B_2$, or $B_3$:

(B1)

(B2)

and

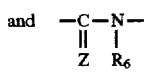  (B3)

in which Z represents oxygen or sulfur and $R_6$ represents hydrogen or a radical chosen from alkyl, cycloalkyl, cycloalkylalkyl, aryl, and arylalkyl, Y represents a radical $Y_1$ chosen from alkyl, alkyl substituted with one or more halogens, alkenyl, alkynyl, cycloalkyl, and cycloalkylalkyl; or Y may also represent a hydrogen when B represents a group $B_1$ or $B_2$, and X represents oxygen, sulfur, or a group

in which $R_7$ represents hydrogen or a radical chosen from alkyl, aryl, substituted aryl, arylalkyl, and substituted aryalkyl; or $R_7$ represents a group of formula —A—B—Y as defined above and, in this case, $R_5$ represents a value chosen from those defined for $R_1$, $R_2$, $R_3$ and $R_4$, as defined above, with the proviso that the compound of formula (I) cannot be N-[2-(1H-pyrrolo[3,2-c]pyrid-3-yl)ethyl]acetamide, and that $R_7$ cannot represent a phenyl when the nitrogen of the pyridine ring of the formula (I) is in the 7-position of the heterocycle, $R_1$ is an alkyl group in the 4-position of the heterocycle, and $R_2$, $R_3$ and $R_4$ represent hydrogens, it being understood that:
 the terms "alkyl" and "alkoxy" denote linear or branched groups containing from 1 to 6 carbon atoms, inclusive,
 the terms "alkenyl" and "alkynyl" denote linear or branched unsaturated groups containing 2 to 6 carbon atoms, inclusive,
 the term "cycloalkyl" denotes a group of 3 to 8 carbon atoms, inclusive,
 the term "aryl" denotes a phenyl, naphthyl, or pyridyl radical,
 the term "substituted" in reference to the expressions "aryl" and "arylalkyl" means that these groups may be substituted on the aromatic rings with one or more radicals chosen from halogen, alkyl, alkoxy, hydroxyl, and alkyl subsitituted with one or more halogens;

its enantiomers and diastereoisomers and its addition salts with a pharmaceutically-acceptable acid or base.

2. A compound of claim 1, selected from those of the following formulae (12) and (13):

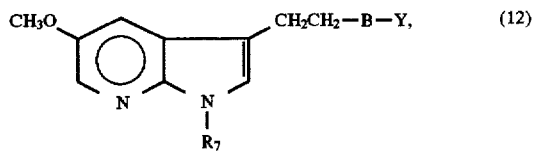

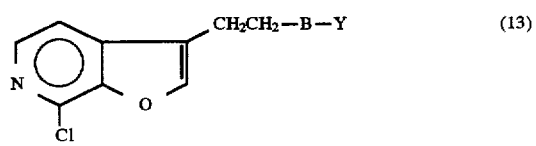

in which $R_7$, B, and Y are as defined in claim 1.

3. A compound as claimed in claim 1, which is N-[2-(5-METHOXY-1-METHYLPYRROLO[2,3-b]PYRID-3-YL)ETHYL]ACETAMIDE.

4. A compound as claimed in claim 1, which is N-[2-(7-CHLOROFURO[2,3-c]PYRID-3-YL)ETHYL]ACETAMIDE.

5. A compound as claimed in claim 1, which is N-[2-(5-METHOXY-1-METHYLPYRROLO[2,3-b]PYRID-3-YL)ETHYL]CYCLOPROPYLCARBOXAMIDE.

6. A compound as claimed in claim 1, which is N-[2-(2-PHENYL-1H-PYRROLO[2,3-b]PYRID-3-YL)ETHYL]ACETAMIDE.

7. A compound as claimed in claim 1, which is N-[2-(5-BROMO-1H-PYRROLO[2,3-b]PYRID-3-YL)ETHYL]ACETAMIDE.

8. A compound as claimed in claim 1, which is N-[2-(5-METHOXYFURO[3,2-b]PYRID-3-YL)ETHYL]ACETAMIDE.

9. A pharmaceutical composition containing a compound of formula (I) as claimed in claim 1, in combination with one or more pharmaceutically-acceptable excipients.

10. A compound as claimed in claim 1, which is N-[2-(5-methoxy-1-methyl-2-phenylpyrrolo[2,3-b]pyrid-3-yl)ethyl]acetamide.

11. A method of treating a mammal afflicted with a melatonin-mediated condition selected from the group consisting of circadian rhythm disorders, sleeping disorders or ovulation disorders, or a melatonin-mediated condition requiring an anxiolytic, antipsychotic, or analgesic, comprising the step of administering to said mammal an effective amount of a compound of claim 1 in order to alleviate said disorder.

* * * * *

UNITED STATES PATENT AND TRADEMARK OFFICE
CERTIFICATE OF CORRECTION

PATENT NO. : 5,714,495
DATED : Feb. 3, 1998
INVENTOR(S): M-C. Viaud, G. Guillaumet, D. Mazeas, H. Vandepoel, P. Renard, B. Pfeiffer, P. Delagrange Page 1 of 3

It is certified that error appears in the above-indentified patent and that said Letters Patent is hereby corrected as shown below:

Column 1, lines 66 and 67: In both instances "an/I" should read -- aryl --.

Column 7, line 33: "Re" should read -- $R_6$ --.

Column 19, line 35: " $CDCl_3$))" should read -- ($CDCl_3$)) --.

Column 23, line 34: Delete "$CH_3O$" in the upper left side of the figure.

Column 42, line 18: Delete the "C" at the end of the line.

Column 42, line 19: Insert -- C -- at the beginning of the line.

Column 46, line 26: Delete "C" at the end of the line.

Column 46, line 27: Insert -- C -- at the beginning of the line.

UNITED STATES PATENT AND TRADEMARK OFFICE
CERTIFICATE OF CORRECTION

PATENT NO. : 5,714,495
DATED : Feb. 3, 1998
INVENTOR(S) : M-C. Viaud, G. Guillaumet, D. Mazeas, H. Vandepoel, P. Renard, B. Pfeiffer, P. Delagrange It is certified that error appears in the above-indentified patent and that said Letters Patent is hereby corrected as shown below:

Column 47, line 45: "anhyddde" should read -- anhydride --.

Column 47, line 57: Delete "C" at the end of the line.

Column 47, line 58: Insert -- C -- at the beginning of the line.

Column 49, line 49: "vadous" should read -- various --.

Column 50, line 61: "Iocomotor" should read -- locomotor --.

Column 51, line 1: "cleady" should read -- clearly --.

Column 53, line 27: Delete "a" before "phenyl".

UNITED STATES PATENT AND TRADEMARK OFFICE
CERTIFICATE OF CORRECTION

PATENT NO. : 5,714,495
DATED : Feb. 3, 1998
INVENTOR(S) : M-C. Viaud, G. Guillaumet, D. Mazeas, H. Vandepoel, P. Renard, B. Pfeiffer, P. Delagrange It is certified that error appears in the above-indentified patent and that said Letters Patent is hereby corrected as shown below:

Column 53, line 34: Delete "from" after "containing".

Column 53, line 45: "rings" should read -- ring --.

Signed and Sealed this

Fourth Day of August, 1998

Attest:

BRUCE LEHMAN

Attesting Officer

Commissioner of Patents and Trademarks